United States Patent [19]
Lundy et al.

[11] Patent Number: 6,043,226
[45] Date of Patent: Mar. 28, 2000

[54] 3,6-KETAL AND ENOL ETHER MACROLIDE ANTIBIOTICS

[75] Inventors: Kristin Marie Lundy, Groton; Hengmiao Cheng, East Lyme; Martha L. Minich, Gales Ferry; Subas Man Sakya, East Lyme; Peter Bertinato, Old Lyme, all of Conn.

[73] Assignee: Pfizer Inc., New York, N.Y.

[21] Appl. No.: 09/257,709

[22] Filed: Feb. 25, 1999

Related U.S. Application Data

[60] Provisional application No. 60/076,630, Mar. 3, 1998.

[51] Int. Cl.$^7$ .............................. A61K 31/70; C07H 17/08

[52] U.S. Cl. .............................. 514/29; 536/7.2; 536/7.4; 536/18.5

[58] Field of Search ........................... 536/7.2, 7.4, 18.5; 514/29

[56] References Cited

U.S. PATENT DOCUMENTS 4,957,905  9/1990  Hunt .......................................... 514/29

*Primary Examiner*—Elli Peselev
*Attorney, Agent, or Firm*—Peter C. Richardson; Paul H. Ginsburg; Jolene W. Appleman

[57] ABSTRACT

This invention relates to compounds of formulas 1 and 2

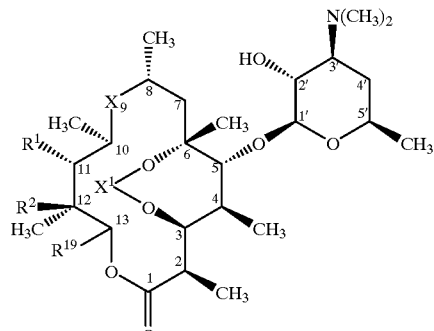

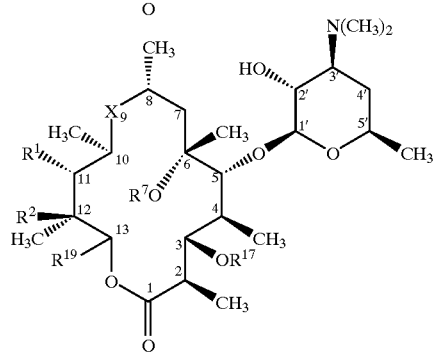

and to pharmaceutically acceptable salts and solvates thereof, wherein X, $X^1$, $R^1$, $R^2$, $R^7$, $R^{17}$ and $R^{19}$ are as defined herein. The compounds of formulas 1 and 2 may be useful in the treatment of bacterial, parasitic and protozoal infections, as well as disorders related to bacterial, parasitic and protozoal infections, in mammals, fish and birds. The invention also relates to pharmaceutical compositions containing the compounds of formula 1 and 2 and to methods of treating bacterial, parasitic and protozoal infections by administering the compounds of formula 1 and 2.

11 Claims, No Drawings

3,6-KETAL AND ENOL ETHER MACROLIDE ANTIBIOTICS

This application claims benefit of Provisional application Ser. No. 60/076,630, filed Mar. 3, 1998.

BACKGROUND OF THE INVENTION

This invention relates to novel macrolide derivatives that may be useful in the treatment of bacterial, parasitic and protozoal infections in mammals, including man, as well as in fish and birds. This invention also relates to pharmaceutical compositions containing the novel compounds and to methods of treating bacterial, parasitic and protozoal infections in mammals, fish and birds by administering the novel compounds to mammals, fish and birds requiring such treatment.

Macrolide antibiotics are known to be useful in the treatment of a broad sprectrum of bacterial infections in mammals, including humans, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. provisional patent application Ser. No. 60/049349, filed Jun. 11, 1997 (Yong-Jin Wu); in U.S. provisional patent application Ser. No. 60/046150, filed May 9, 1997 (Yong-Jin Wu); in U.S. provisional patent application Ser. No. 60/063676, filed Oct. 29, 1997 (Yong-Jin Wu); U.S. provisional patent application Ser. No. 60/063161, filed Oct. 29, 1997 (Yong-Jin Wu); U.S. provisional patent application Ser. No. 60/054866, filed Aug. 6, 1997 (Wei-Guo Su, Bingwei V. Yang, Robert G. Linde, Katherine E. Brighty, Hiroko Masamune, Yong-Jin Wu, Takushi Kaneko and Paul R. McGuirk); U.S. provisional patent application Ser. No. 60/049348, filed Jun. 11, 1997 (Brian S. Bronk, Michael A. Letavic, Takushi Kaneko, Bingwei V. Yang, Hengmiao Cheng, Edward Glazer); International Application No. PCT/GB97/01810 filed Jul. 4, 1997 (Peter Francis Leadlay, James Staunton, Jesus Cortes and Michael Stephen Pacey); International Application No. PCT/GB97/01819, filed Jul. 4, 1997 (Peter Francis Leadlay, James Staunton, and Jesus Cortes); United States provisional patent application entitled "Novel Macrolides", filed Jan. 2, 1998 (John P. Dirlam); and U.S. provisional patent application entitled "Novel Erythromycin Derivatives", filed Jan. 2, 1998 (Yong-Jin Wu); all of which are incorporated herein by reference in their entirety. Like azithromycin and other macrolide antibiotics, the novel macrolide compounds of the present invention possess potent activity against various bacterial infections as described below.

SUMMARY OF THE INVENTION

The present invention relates to compounds of formulas 1 and 2

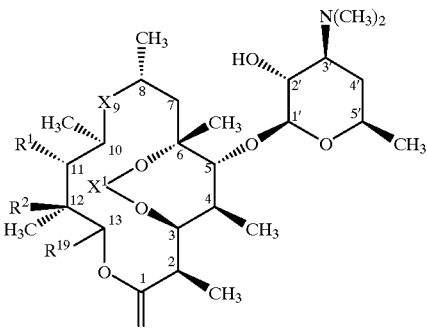

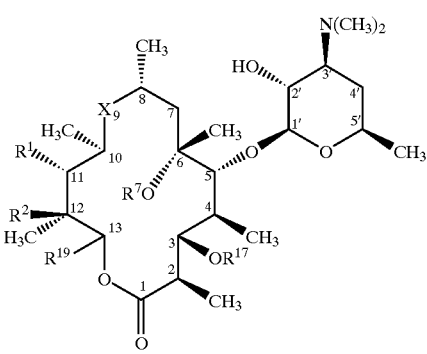

and to pharmaceutically acceptable salts and solvates thereof, wherein:

X is —CH(—NR$^9$R$^{10}$)—, —CH(OR$^3$)—, —C(O)—, —CH$_2$NR$^6$—, —NR$^6$CH$_2$—, or —C(=NR$^5$)—, wherein the first dash of each of the foregoing X groups is attached to the C-10 carbon of the compounds of formulas 1 and 2 and the last dash of each group is attached to the C-8 carbon of the compounds of formulas 1 and 2;

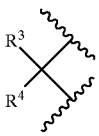

R$^1$ and R$^2$ are each OH;
or R$^2$ is O and R$^1$ is X$^2$, and they are taken together as follows:

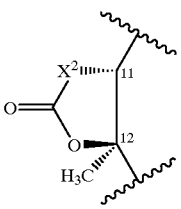

wherein X$^2$ is O, —N(R$^7$)—, or —N(NR$^7$R$^8$)—;
each R$^3$ and R$^{3'}$ is independently selected from the group consisting of H, C$_1$-C$_6$ alkyl, —(CH$_2$)$_m$(C$_6$-C$_{10}$ aryl), and —(CH$_2$)$_m$(4–10 membered heterocyclic), wherein m is an integer ranging from 0 to 4 and the foregoing R$^3$ groups are optionally substituted by 1 to 3 R$^{13}$ groups;

$R^4$ is selected from the group of substituents provided in the definition of $R^3$ or $R^4$ is —$OR^7$;

or $R^3$ and $R^4$ are taken together with the carbon to which each is attached to form a ring defined by $X^3$, $X^4$ and $X^5$ as follows

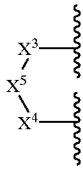

wherein $X^3$ and $X^4$ are each independently —$(CHR^{16})_n$— wherein n is an integer ranging from 1 to 4;

$X^5$ is S, O, —$CHR^6$—, or —$N(R^6)$—;

$R^5$ is hydroxy, $C_1$–$C_6$ alkyl, $C_1$–$C_6$ alkoxy, —$(CH_2)_m(C_6$–$C_{10}$ aryl), —$(CH_2)_m$(4–10 membered heterocyclic), or —$(CH_2)_mO(CH_2)_zOR^7$, wherein m is an integer ranging from 0 to 4 and z is an integer ranging from 2 to 6, and the foregoing $R^5$ groups, except hydroxy, are optionally substituted by 1 to 3 $R^{13}$ groups;

$R^6$ is H, hydroxy, formyl, $C_1$–$C_{10}$ alkoxy, $C_1$–$C_{10}$ alkyl, $C_2$–$C_{10}$ alkenyl, —$SO_2(C_1$–$C_{10}$ alkyl), —$(CH_2)_mC(O)CH_2OC(O)(C_1$–$C_{10}$ alkyl), —$(CH_2)_mC(O)(CH_2)_tNR^{11}R^{12}$, —$(CH_2)_tC(O)(C_1$–$C_{10}$ alkyl), —$(CH_2)_mC(O)(CH_2)_tC(O)(C_1$–$C_{10}$ alkyl), —$(CH_2)_mC(O)(CH_2)_tO(C_1$–$C_{10}$ alkyl), —$(CH_2)_mC(O)(CH_2)_tO(C_2$–$C_{10}$ alkenyl), —$(CH_2)_t(C_6$–$C_{10}$ aryl), —$(CH_2)_t$(4–10 membered heterocylic), —$C(O)(CH_2)_mC(O)(CH_2)_q(C_6$–$C_{10}$ aryl), —$C(O)(CH_2)_mC(O)(CH_2)_q$(4–10 membered heterocyclic), —$(CH_2)_mC(O)(CH_2)_q(C_6$–$C_{10}$ aryl), —$(CH_2)_mC(O)(CH_2)_q$(4–10 membered heterocyclic), —$(CH_2)_qC(O)(CH_2)_mO(CH_2)_t(C_6$–$C_{10}$ aryl), —$(CH_2)_qC(O)(CH_2)_mO(CH_2)_t$(4–10 membered heterocyclic), —$(CH_2)_tO(CH_2)_m(C_6$–$C_{10}$ aryl), —$(CH_2)_tO(CH_2)_m$(4–10 membered heterocyclic), —$(CH_2)_mP(O)R^3R^{16}$, —$SO_2(CH_2)_t(C_6$–$C_{10}$ aryl), or —$SO_2(CH_2)_t$(4–10 membered heterocyclic), —$(CH_2)_mC(S)(CH_2)_tNR^{11}R^{12}$, wherein m is an integer ranging from 0 to 4, q and t are each independently an integer ranging from 0 to 5, the —$(CH_2)_q$— moiety of the above $R^6$ groups optionally includes a carbon-carbon double bond where q is 2 or greater, the heterocyclic moieties of the above $R^6$ groups optionally include an oxo (O) group on the ring system, and the foregoing $R^6$ groups, except H, formyl and hydroxy, are optionally substituted by 1 to 3 $R^{13}$ groups;

each $R^7$ and $R^8$ is independently H or $C_1$—$C_6$ alkyl;

$R^9$ and $R^{10}$ are each independently selected from H, $C_1$–$C_6$ alkyl, —$C(=NR^5)NR^7R^8$, and —$C(O)R^7$, or $R^9$ and $R^{10}$ are taken together to form =CH$(CH_2)_m(C_6$–$C_{10}$ aryl), =CH$(CH_2)_m$(4–10 membered heterocyclic), =$CR^7R^8$, or =$C(R^7)C(O)OR^8$, wherein m is an integer ranging from 0 to 4, and the alkyl, aryl and heterocyclic moieties of the foregoing $R^9$ and $R^{10}$ groups are optionally substituted by 1 to 3 $R^{13}$ groups;

$R^{11}$ and $R^{12}$ are each independently selected from H, $C_1$–$C_{10}$ alkyl, $C_2$–$C_{10}$ alkenyl, —$C(O)(C_1$–$C_{10}$ alkyl), —$(CH_2)_m(C_6$–$C_{10}$ aryl), —$C(O)(CH_2)_m(C_6$–$C_{10}$ aryl), —$(CH_2)_m$(4–10 membered heterocyclic), and —$C(O)(CH_2)_m$(4–10 membered heterocyclic), wherein m is an integer ranging from 0 to 4, and the foregoing $R^{11}$ and $R^{12}$ groups, except H, are optionally substituted by 1 to 3 $R^{13}$ groups;

each $R^{13}$ is independently selected from halo, cyano, nitro, trifluoromethyl, azido, —$C(O)R^{16}$, —$C(O)OR^{16}$, —$OC(O)R^{16}$, —$OC(O)OR^{16}$, —$NR^{14}C(O)R^{15}$, —$C(O)NR^{14}R^{15}$, —$NR^{14}R^{15}$, hydroxy, $C_1$–$C_6$ alkyl, —$N(SO_2R^{16})_2$, —$NR^{14}SO_2R^{16}$, —$S(O)_j(C_1$–$C_6$ alkyl) where j is an integer ranging from 0 to 2, $C_1$–$C_6$ alkoxy, —$(CH_2)_m(C_6$–$C_{10}$ aryl), and —$(CH_2)_m$(4–10 membered heterocyclic), wherein m is an integer ranging from 0 to 4, and the alkyl, alkoxy, aryl and heterocyclic moieties of the above $R^{13}$ substiuents are optionally substituted by 1 to 3 substituents independently selected from halo, cyano, nitro, trifluoromethyl, azido, —$C(O)R^{16}$, —$C(O)OR^{16}$, —$CO(O)R^{16}$, —$OC(O)OR^{16}$, —$NR^{14}C(O)R^{15}$, —$C(O)NR^{14}R^{15}$, —$NR^{14}R^{15}$, hydroxy, $C_1$–$C_6$ alkyl, and $C_1$–$C_6$ alkoxy;

each $R^{14}$ and $R^{15}$ is independently H, —$OR^7$, $C_1$–$C_6$ alkyl, —$(CH_2)_m(C_6$–$C_{10}$ aryl), or —$(CH_2)_m$(4–10 membered heterocyclic), wherein m is an integer ranging from 0 to 4, with the proviso that where $R^{14}$ and $R^{15}$ are both attached to the same nitrogen, then $R^{14}$ and $R^{15}$ are not both —$OR^7$;

each $R^{16}$ is independently selected from H, $C_1$–$C_{10}$ alkyl, —$(CH_2)_m(C_6$–$C_{10}$ aryl), and —$(CH_2)_m$(4–10 membered heterocyclic), wherein m is an integer ranging from 0 to 4; and, $R^{17}$ is selected from the group of substituents provided in the definition of $R^{18}$ or $R^{17}$ is a group of the formula

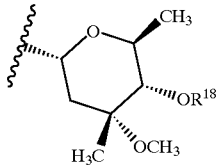

$R^{18}$ is —$CR^3$=$CR^3R^4$ or a group of the formula

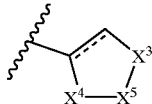

wherein the dashed line represents an optional double bond; and $R^{19}$ is ethyl, an alpha-branched $C_3$–$C_6$ alkyl, $C_2$–$C_6$ alkenyl, $C_2$–$C_6$ alkynyl, ($C_1$–$C_6$ alkoxy) $C_1$–$C_6$ alkyl, ($C_1$–$C_6$ alkylthio)$C_1$–$C_6$ alkyl, ($C_5$–$C_8$ cycloalkyl)($C_2$–$C_5$ alpha branched alkyl)—, $C_3$–$C_8$ cycloalkyl, $C_5$–$C_8$ cycloalkenyl, 3–6 membered O or S containing heterocyclic group, or phenyl, wherein each of the foregoing $R^{19}$ groups may be substituted by 1 to 3 substituents independently selected from hydroxy, halo and $C_1$–$C_4$ alkyl.

More specific embodiments of this invention include compounds of formula 1 wherein $R^{19}$ is ethyl, X is —NR⁶CH₂— or —CH₂NR⁶—, where $R^6$ is H or methyl, $R^1$ and $R^2$ are both hydroxy, and $X^1$ is the following cyclic group:

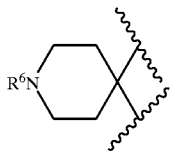

wherein $R^6$ is H, hydroxy, hydroxy substituted $C_1-C_{10}$ alkyl, formyl, $C_1-C_{10}$ alkoxy, —SO₂($C_1-C_4$ alkyl), —(CH₂)$_m$C(O)($C_1-C_{10}$ alkyl), —(CH₂)$_m$C(O)CH₂OC(O)($C_1-C_{10}$ alkyl), —(CH₂)$_m$C(O)CH₂O($C_1-C_{10}$ alkyl), —(CH₂)$_m$C(O)(CH₂)$_q$($C_6-C_{10}$ aryl), —(CH₂)$_m$C(O)(CH₂)$_q$(4–10 membered heterocyclic), —(CH₂)$_t$(4–10 membered heterocyclic), or —(CH₂)$_t$($C_6-C_{10}$ aryl), where m, q and t are as defined above in the definition of $R^6$. More preferred compounds include those wherein m, q and t are each independently 0 or 1. Other preferred compounds include those wherein $R^6$ in the above piperidine group is selected from: —C(O)CH₂CH₃, —C(O)CH₂OCH₃, —C(O)H, —C(O)CH₂OH, —C(O)CH₂OC(O)CH₃, —C(O)CH₃, -4-chlorobenzyl, 2-pyridylmethyl, 4-acetamidobenzyl, 4-hydroxy-3-methoxybenzyl, 3-hydroxy-4-methoxybenzyl, 2-hydroxyethyl, —C(O)CH₂N(CH₃)₂, 4-quinolinylmethyl, 2-quinolinylmethyl, —C(O)CH₂OC(O)CH₃, —SO₂CH₂CH₃, —SO₂CH(CH₃)₂, 2-furoyl, benzoyl, 1-methyl-2-pyrrolylcarbonyl, 2-pyrazinylcarbonyl, 2-pyridylcarbonyl, 2-quinolinylcarbonyl, 3-pyridylcarbonyl, 3-cinnolinecarbonyl, 3-quinolinylcarbonyl, 4-benzyloxycarbonyl-2-fluorophenyl, and

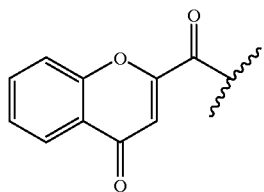

The invention also relates to a pharmaceutical composition for the treatment of a bacterial, parasitic or protozoal infection, or a disorder related to a bacterial, parasitic or protozoal infection, in a mammal, fish, or bird which comprises a therapeutically effective amount of a compound of formula 1 or 2, or a pharmaceutically acceptable salt or solvate thereof, and a pharmaceutically acceptable carrier.

The invention also relates to a method of treating a bacterial, parasitic or protozoal infection, or a disorder related to a bacterial, parasitic or protozoal infection, in a mammal, fish, or bird which comprises administering to said mammal, fish or bird a therapeutically effective amount of a compound of formula 1 or 2 or a pharmaceutically acceptable salt or solvate thereof.

The invention also relates to a pharmaceutical composition for the treatment of cancer, in particular non-small cell lung cancer, in a mammal, in particular a human, which comprises a therapeutically effective amount of a compound of formula 1 or 2, or a pharmaceutically acceptable salt or solvate thereof, and a pharmaceutically acceptable carrier.

The invention also relates to a method of treating cancer, in particular non-small cell lung cancer, in a mammal, which comprises administering to said mammal a therapeutically effective amount of a compound of formula 1 or 2 or a pharmaceutically acceptable salt or solvate thereof.

The invention also relates to a method of preparing a compounds of the formula 1 or 5, or both 1 and 5

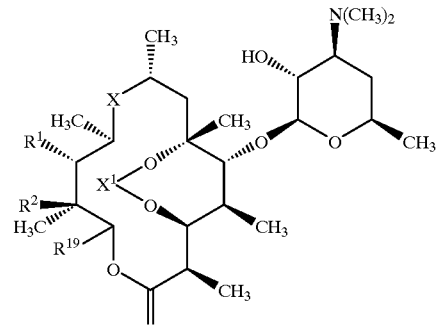

1

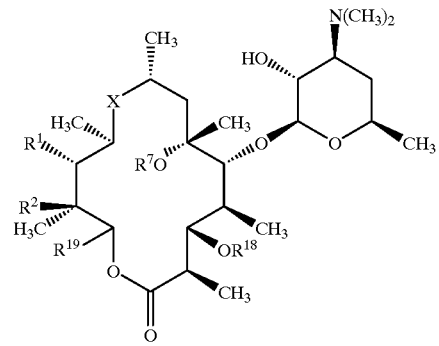

5 wherein X, $X^1$, $R^1$, $R^2$, $R^7$, $R^{18}$ and $R^{19}$ are as defined above, which comprises treating a compound of the formula

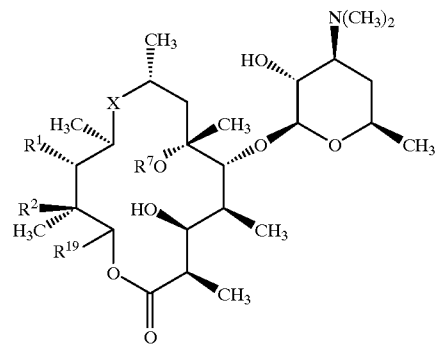

3 with a compound of the formula $R^3C(O)R^{3'}$, $H_3CO(R^3)C=CR^{3'}R^{3''}$ (wherein $R^{3''}$ is defined as $R^3$ and $R^{3'}$ which are defined as provided above), or

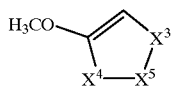

in an aprotic solvent, preferably methylene chloride, in the presence of pyridinium p-toluenesulfonate and/or p-toluenesulfonic acid monohydrate. In this process, both compounds 1 and 5 may be formed. The compound of formula 5 that will be formed will be one wherein $R^{18}$ is —C($R^3$)=$CR^{3'}R^{3"}$ or a group of the formula

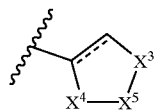

wherein the dashed line represents an optional double bond and $X^3$, $X^4$ and $X^5$ are as defined above.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial, parasitic or protozoal infection", or "disorder related to a bacterial, parasitic or protozoal infection" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or Peptostreptococcus spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by S. aureus (food poisoning and toxic shock syndrome), or Groups A, B, and C streptococci; ulcers related to infection by Helicobacter pylori, systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium* perfringens or Bacteroides spp.; and atherosclerosis or cardiovascular disease related to infection by *Helicobacter pylori* or *Chiamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or Bordetella spp.; cow enteric disease related to infection by *E. Coli* or protozoa (i.e., coccidia, cryptosporidia, etc.); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodysinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxelia bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius*, coagulase neg. Staph. or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group, and for said alkyl group to include a carbon-carbon double or triple bond at least two carbon atoms are required in said alkyl group. Where said alkyl moiety is defined as $C_1$–$C_{10}$ alkyl, this group includes $C_6$–$C_{10}$ bicyclo groups such as a bicyclo [3.1.1]heptylmethyl group.

The term "aryl", as used herein, unless otherwise indicated, includes an organic radical derived from an aromatic hydrocarbon by removal of one hydrogen, such as phenyl or naphthyl, as well as benzo-fused carbocyclic moieties such as 5,6,7,8-tetrahydro-naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or two oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Non-aromatic heterocyclic groups include saturated and partially un-saturated ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include chroman, benzodihydrofuran and benzimidazolyl. Heterocyclic groups having one or two oxo moieties include phthalimide and uracil.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e, 1,1'1-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The preparation of the compounds of the present invention is illustrated in the following Scheme. In the following Scheme, unless otherwise indicated, X, $R^1$, $R^2$, and $X^1$ are as defined above.

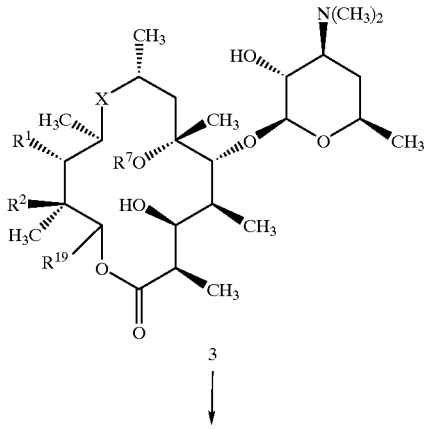

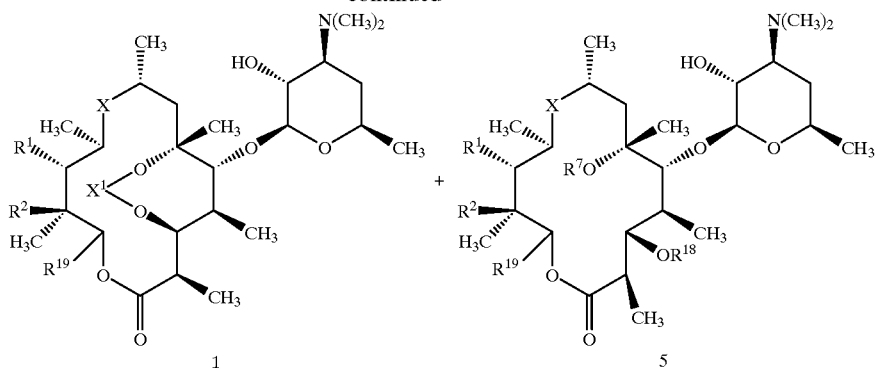

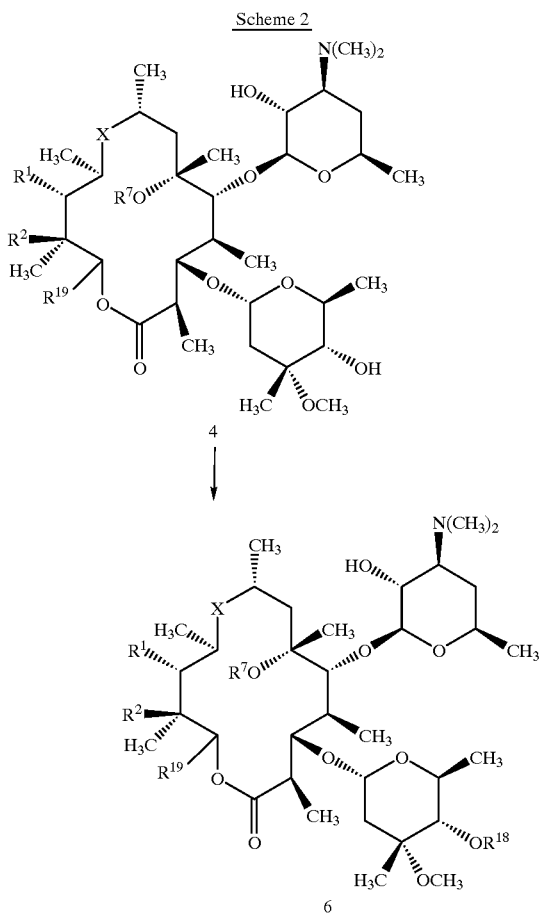

This invention uses a variety of macrolide templates as starting materials. They include azalides such as N9a-desmethyl azithromycin, azithromycin, erythromycin, clarithromycin, erythromycylamine as well as their analogs. Azithromycin can be prepared according to methods described in U.S. Pat. Nos. 4,474,768 and 4,517,359, referred to above. Erythromycin can be prepared, or isolated, according to methods described in U.S. Pat. Nos. 2,653,899 and 2,823,203. Clarithromycin can be prepared according to methods described in U.S. Pat. No. 4,331,803. The macrolide template corresponding to the compound of formula 1 or 2 wherein $R^1$ and $R^2$ are taken together, $R^1$ is —N($R^7$)— and $R^2$ is O, and X is —C(O)— can be prepared according to methods described in Journal of Organic Chemistry 53, 2340 (1988). The starting materials referred to in Schemes 1 and 2 above where $R^{19}$ is a moiety other than ethyl within the definition of $R^{19}$ above may be prepared as described in PCT published applications WO 98/01571 (Biotica Tech. Ltd. and Pfizer Inc.) and WO 98/01546 (assigned to Biotica Tech. Ltd.). The above macrolide templates may be converted to the corresponding descladinose templates by treating the compounds with acetyl chloride in methanol at approximately ambient temperature. These starting materials may or may not require proper functional group protection before various modifications can take place, and deprotection after desired modifications are complete. The most commonly used protecting groups for amino moieties in the macrolide compounds of this invention are benzyloxycarbonyl (Cbz) and t-butyloxycarbonyl (Boc) groups. Hydroxyl groups are generally protected as acetates or Cbz carbonates.

To protect amino moieties, in particular the C-9 amino moiety of erythromycylamine, the macrolide is treated with t-butyl dicarbonate in anhydrous tetrahydrofuran (THF), or benzyloxycarbonyl N-hydroxysuccinimide ester (Cbz-OSu), to protect the C-9 amino group as its t-butyl or benzyl carbamate. The Boc group is normally removed either by acid treatment or by following a two step procedure as follows: (1) treatment with an excess amount (10 equivalents) of trimethylsilyl triflate in dichloromethane in the presence of 2,6-lutidine, and (2) desilylation with tetra-n-butylammonium fluoride in THF. The Cbz groups can be removed by conventional catalytic hydrogenation.

The C-2' hydroxyl group is a reactive hydroxyl group among the numerous hydroxyl groups present in macrolide compounds of the type claimed herein. The C-2' hydroxyl group is selectively protected by treating the compound with one equivalent of acetic anhydride in dichloromethane in the absence of external base. This process selectively converts the C-2' hydroxyl group into the corresponding acetate. The hydroxyl protecting group can be removed by treating the compound with methanol at a temperature ranging from about 0° C. to about 65° C. for 2 to 48 hours.

Alternatively, where the starting material for the preparation of the compounds of this invention is erythromycylamine or $N_{9a}$-desmethyl azithromycin, these compounds can be treated with an excess of benzylchloroformate in THF/water at a pH of about 9 to provide N-9,2'-bis-Cbz protected erythromycylamine or $N_{9a}$desmethyl azithromycin. In this process, the amino group and the C-2' hydroxyl group can be protected in one step.

With reference to the above Scheme 1, the compound of formula 3 may be converted to the compounds of formulas 1 and 5 by treating the compound of formula 3 with a compound of the formula $R^3C(O)R^{3'}$, $H_3CO(R^3)C=CR^{3''}R^{3'''}$ (wherein $R^{3'''}$ is defined as $R^3$ and $R^{3'}$ which are defined as provided above), or

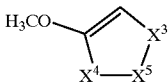

in an aprotic solvent, preferably methylene chloride, in the presence of pyridinium p-toluenesulfonate and/or p-toluenesulfonic acid monohydrate at ambient temperature for a period of about 1 hour to 5 days. In this process, both compounds 1 and 5 may be formed. The compound of formula 5 that will be formed will be one wherein $R^{18}$ is —$C(R^3)=CR^{3''}R^{3'''}$ or a group of the formula

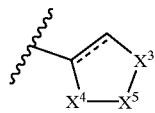

wherein the dashed line represents an optional double bond and $X^3$, $X^4$ and $X^5$ are as defined above.

Further, in this process, the following 4-azacyclohexyl moiety may be introduced as the $X^1$ group in the compound of formula 1

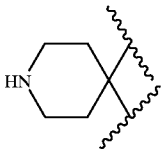

The nitrogen of the above $X^1$ group may be further modified to introduce various $R^6$ substituents according to various methods that would be familiar to those skilled in the art. In one method, a compound of formula 1 which includes the above 4-azacyclohexyl moiety may be treated with a compound of the formula $R^6$—Q, wherein Q is a leaving group, preferably chloro or bromo, and is connected to an alkyl moiety of an appropriate $R^6$ group (such as benzyl chloride), in an aprotic solvent, preferably methylene chloride, in the presence of triethylamine or pyridine at ambient temperature for a period of about 24 to 48 hours, or by reductive amination with formaldehyde or hydrogen and palladium on carbon. In another method, the nitrogen of the above 4-azacyclohexyl group may be modified by reductive amination such as by treating the compound with an aldehyde of the formula $R^6$—C(O)H, wherein $R^6$ includes various moieties that may be attached to the nitrogen through an alkyl group, in an aprotic solvent, preferably methylene chloride, in the presence of sodium sulfate, acetic acid and sodium triacetoxyborohydride at ambient temperature for about 30 minutes to 48 hours. This method results in the nitrogen being substituted with a group of the formula $R^6CH_2$—. In another method, the nitrogen of the above 4-azacyclohexyl group may be modified by coupling with an acid of the formula $R^6$—C(O)OH, wherein $R^6$ includes various moieties that may be attached to the nitrogen through a carbonyl —C(O)— group, in an aprotic solvent, preferably methylene chloride, in the presence of triethylamine or diisopropylethylamine, 1-hydroxybenzotriazole, and 1-ethyl-3-(3-dimethylaminopropyl)carbodiimide hydrochloride. This method results in the nitrogen being substituted with a group of the formula $R^6C(O)$—. Other groups may be introduced at this nitrogen as described below in methods A–AP. For instance, a sulfonamide moiety may be produced as described in method 1, a carbamate moiety may be produced as described in method M, and a urea moiety may be produced as described in method Q.

Scheme 2 illustrates the preparation of a compound of formula 6. In this process, the starting material is a compound of formula 4 rather than the corresponding descladinose macrolide template. The compound of formula 4 is treated with a compound of the formula $R^3C(O)R^{3'}$, $H_3CO(R^3)C=CR^{3''}R^{3'''}$ (wherein $R^{3'''}$ is defined as $R^3$ and $R^{3'}$ are defined above), or

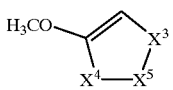

according to substantially the same conditions as described above for Scheme 1 to provide the $R^{18}$ groups described above with respect to compound 5 in Scheme 1.

Specific preparations that have been employed to prepare the compounds of formulas 1 and 2 are described below as Methods A–AP. In the following preparations, the following abbreviations may be used: Et (ethyl), Me (methyl), and HOBT (1-hydroxybenzotriazole hydrate), THF (tetrahydrofuran), DMF (N,N-dimethylformamide), and EDC (1-(3-dimethylaminopropyl)-3-ethylcarbodiimide hydrochloride).

Method A

Descladinose-azithromcin-3,6-cyclohexml ketal; O3,O6-cyclohexylidenedescladinose-azithromycin; and Descladinose azithromycin-3-(1-cyclohexenyl) ether To a solution of descladinose azithromycin (1.33 g, 2 mmol) in dry methylene chloride (100 ml) was added 1-methoxycyclohexene (13.44 g, 120 mmol) and pyridinium p-toluenesulfonate (3.0 g, 12 mmol). The solution was stirred under nitrogen at room temperature for four days. Dilute potassium carbonate solution was added, and the organic layer separated, washed with brine, dried over sodium sulfate, and filtered. The solvent was removed in vacuo, and the residue purified by flash chromatography (75 g silica, 0.8% concentrated ammonium hydroxide in 8% methanol/methylene chloride) to give descladinose-azithromycin-3,6-cyclohexyl ketal (400 mg, 0.59 mmol, 30%), mass spectrum 672. Descladinose azithromycin-3-(1-cyclohexenyl) ether was also isolated (120 mg, 0.18 mmol, 9% yield), mass spectrum 672.

Method B

N-Desmethyl-descladinose-azithromycin-3,6-(4-oxocyclohexyl) ketal and N-Desmethyl-descladinose azithromycin-3-(4-[5,6-dihydropyranyl]) ether To a solution of of N-desmethyl-descladinose azithromycin (5.77 g, 10 mmol) in dry methylene chloride (200 ml) was added 5,6-dihydro-4-methoxy-pyran (22.8 g, 200 mmol), pyridinium p-toluenesulfonate (15.08 g, 60 mmol) and p-toluenesulfonic acid monohydrate (4.0 g, 21 mmol). The mixture was stirred at room temperature under nitrogen for 9.5 hours, washed with dilute potassium carbonate and brine, and filtered. The filtrates from four identical reactions were combined and concentrated under reduced pressure. The residue was divided into three equal portions and each was purified by flash chromatography (1 kg silica, 0.8% concentrated ammonium hydroxide in 8% methanol/ methylene chloride). Impure fractions were re-chromatographed on 450 g silica with the same solvent, to give a total of 15.95 g (24.2 mmol, 60.5%) of N-desmethyl-descladinose-azithromycin-3,6-(4-oxocyclohexyl) ketal, mass spectrum 659.5. N-Desmethyl-descladinose azithromycin-3-(4-[5,6-dihydropyranyl]) ether was also isolated (1.97 g, 2.99 mmol, 7.5% yield), mass spectrum 659.5.

Method C

Descladinose azithromycin-3,6-(4-acetyl-4-azacyclohexyl) ketal

To a solution of descladinose azithromycin (950 mg, 1.62 mmol) in methylene chloride (90 ml) was added 1-acetyl-4-methoxy-1,2,3,6-tetrahydropyridine (7.55 g, 48.7 mmol) and p-toluenesulfonic acid monohydrate (941 mg, 4.95 mmol). The mixture was stirred at room temperature under nitrogen for four days, diluted with methylene chloride, washed with dilute potassium carbonate and brine, dried over sodium sulfate, filtered, and concentrated under reduced pressure. The residue was purified by successive silica gel flash chromatography (150 g silica with 0.3:2:8:10 concentrated ammonium hydroxide/methanol/acetone/benzene, 85 g silica with 25:1 acetonitrile/concentrated ammonium hydroxide, 35 g silica with 0.6% concentrated ammonium hydroxide in 6% methanol/methylene chloride) to give the title compound (310 mg, 26.8% yield), mass spectrum 714.5.

Method D

Descladinose azithromycin-3,6-(4-carbobenzyloxy-4-azacyclohexyl) ketal

To a solution of of descladinose azithromycin (960 mg, 1.62 mmol) in methylene chloride (60 ml) was added 1-carbobenzyloxy-4-methoxy-1,2,3,6-tetrahydropyridine (12 g, 48.6 mmol), pyridinium p-toluenesulfonate (2.44 g, 9.72 mmol) and p-toluenesulfonic acid monohydrate (616 mg, 3.24 mmol). The mixture was stirred at room temperature two days, diluted with methylene chloride, washed with dilute potassium carbonate and brine, dried over sodium sulfate, filtered, and concentrated under reduced pressure. The residue was purified by flash chromatography (100 g silica, 0.3/6/100 concentrated ammonium hydroxide/methanol/methylene chloride) to give the title compound (672 mg, 51.5% yield), mass spectrum 807.8.

Method E

Descladinose-azithromycin-3,6-(4-thiocyclohexyl) ketal

To a solution of of descladinose azithromycin (443 mg, 0.75 mmol) in dry methylene chloride (30 ml) was added 5,6-dihydro4-methoxy-thiopyran (2.13 g of 72% mixture with the thioketone, est. 11.7 mmol), pyridinium p-toluenesulfonate (1.13 g, 4.5 mmol) and p-toluenesulfonic acid monohydrate (299 mg, 1.575 mmol). The mixture was stirred at room temperature under nitrogen for 24 hours, washed with dilute potassium carbonate and brine, and filtered. The filtrate was concentrated under reduced pressure and purified by flash chromatography (60 g silica, 0.6% concentrated ammonium hydroxide in 6% methanol/methylene chloride) to give the title compound (352 mg, 68% yield, mass spectrum 689.4).

Method F

N-Desmethyl-descladinose azithromycin-3,6-(4-acetyl-4-azacyclohexyl) ketal

To a solution of N-desmethyl-descladinose azithromycin 36.67g, 63.55 mmol) in methylene chloride (1400 ml) was added 1-acetyl-4-methoxy-1,2,3,6-tetrahydropyridine (197 g, 1.271 mol), pyridinium p-toluenesulfonate (95.82 g, 0.381 mol) and p-toluenesulfonic acid monohydrate (33.85 g, 0.178 mol). The mixture was stirred at room temperature under nitrogen four days.

The mixture was diluted with methylene chloride (1.5 L), washed twice with dilute potassium carbonate (1 L) and then brine (500 ml), dried over sodium sulfate, filtered, and concentrated under reduced pressure. The residue was purified by reverse phase prep HPLC with the following conditions. A 100×500 mm column packed with 15 $\mu$m Inertsil C-8 gel was equilibrated to a stable baseline with 100% (0.050M NH40Ac+0.1% NH4OH; "buffer") at 400 ml per minute. The crude residue was converted to the citric acid salt in 200 ml of water. The clear solution was loaded onto the column using a sample loading pump. This column was eluted with 100% buffer for 2 minutes, followed by a gradient from 100% buffer to 20% buffer and 80% $CH_3CN$ in 80 minutes. The detector was set at 230 nm. Fractions collected were analyzed by reverse phase HPLC. Fractions >97% purity were combined and concentrated to remove $CH_3CN$. $NaHCO_3$ was added and the product extracted with 2×21 $CHCl_3$. The combined organic layers were dried over $Na_2SO_4$ and concentrated to a white amorphous solid (27.5 g, 39.2 mmol, 61.7%), mass spectrum 700.3.

Alternatively, the product may be obtained with an extractive workup.

After the reaction was judged to be complete, the crude reaction mixture was transferred to a separatory funnel and was washed with an equal volume of 10% $K_2CO_3$. The aqueous phase was discarded, the organic phase was concentrated to low volume and was azeotroped several times with toluene to remove pyridine. The thick brown liquid was then suspended in water (for a typical 300 gram reaction done in 15 liters of $CH_2Cl_2$, 10 liters of water was used) and adjusted to pH 5.0 with $H_3PO_4$. The aqueous layer was washed with $CHCl_3$ (4×41). The pH was adjusted to pH 8.0 with $NaHCO_3$ and the product was extracted with 2×4 liters $CH_3Cl_2$. The combined organic layers were dried over $NaSO_4$, filtered and concentrated to a bright yellow solid. The recovery at this point was approximately equal to the weight of the descladinose azalide starting material.

The enol ether side product in the crude solid was hydrolysed as follows. 100 grams of solid was dissolved in 1600 ml of THF. To the solution was added 400 ml 1N HCL and the reaction was stirred while monitoring the reaction for the disappearance of enol ether. After the reaction was complete (~120–180 minutes at room temperature) enough $NaHCO_3$ was added to neutralize the HCL. The solution was concentrated to remove THF and if needed enough $NaHCO_3$ was added until a pH of 8 was reached. The solution was extracted with 2×500 ml $CH_2Cl_2$. Organic layers were combined, dried over $Na_2SO_4$ and concentrated to a yellow foam, 73.7 grams.

For the final step, the solid was dissolved in 3 liters of 1:1 chloroform:dichloroethane and placed in a 6 liter Erlenmeyer flask. To the stirred solution was added 3 liters of 0.050M $NH_4OAc+0.1\%$ TFA, and the mixture was stirred for 1 minute. The layers are separated, and the lower (organic) layer was dried over $Na_2SO_4$ and concentrated to a white foam (51.50 grams, >99% pure by HPLC).

Method G

Descladinose azithromycin-3,6-(4-azacyclohexyl) ketal

To a solution of descladinose azithromycin-3,6-(4-carbobenzyloxy-4-azacyclohexyl) ketal (460 mg, 0.57 mmol) in isopropanol (20 ml) in a Parr bottle was added 10% palladium on carbon (190 mg). The mixture was agitated under 52 psi hydrogen gas for two days, filtered, and concentrated under reduced pressure. The residue was purified by flash chromatography (20 g silica, 1/10/90 concentrated ammonium hydroxide/methanol/methylene chloride) to give the title compound (330 mg, 86.2% yield), mass spectrum 672.4.

Method H
Descladinose azithromycin-3,6-(4-methyl-4-azacyclohexyl) ketal

To a solution of descladinose azithromycin-3,6-(4-azacyclohexyl) ketal (140 mg, 0.21 mmol) in acetonitrile (17 ml) was added a solution of sodium acetate trihydrate (286 mg, 2.1 mmol), acetic acid (126 mg, 0.12 ml, 2.1 mmol), and 37% aqueous formaldehyde (0.47 ml, 189 mg as formaldehyde, 6.3 mmol) in water (12 ml). The mixture was stirred one hour at room temperature, and sodium cyanoborohydride (39.6 mg, 0.63 mmol) was added. The mixture was stirred an additional two hours, most of the acetonitrile was removed under reduced pressure, and the residue was poured into dilute potassium carbonate, extracted into methylene chloride, dried over sodium sulfate, filtered, and concentrated under reduced pressure. The residue was purified by flash chromatography (5 g silica, 1% concentrated ammonium hydroxide in 10% methanol/methylene chloride) to give the title compound (93 mg, 64.6% yield), mass spectrum 686.5.

Method I
Descladinose azithromycin-3,6-(4-methanesulfonyl-4-azacyclohexyl) ketal To a solution of descladinose azithromycin-3,6-(4-azacyclohexyl) ketal (200 mg, 0.298 mmol) and triethylamine (60.3 mg, 0.083 ml, 0.596 mmol) in methylene chloride (2 ml) under nitrogen at −78° C. was added methanesulfonyl chloride (37.5 mg, 0.025 ml, 0.328 mmol) dropwise over two minutes. The mixture was stirred five minutes at −78° C. and allowed to warm to room temperature. After an additional hour of stirring, the mixture was diluted with methylene chloride, washed with dilute potassium carbonate and brine, dried over sodium sulfate, filtered, and evaporated. The residue was purified by flash chromatography (20 g silica, 0.6% concentrated ammonium hydroxide in 6% methanol/methylene chloride) to give the title compound (135 mg, 60.4% yield), mass spectrum 750.5.

Method J
Descladinose azithromycin-3,6-(4-butanesulfonyl-4-azacyclohexyl) ketal

To a solution of descladinose azithromycin-3,6-(4-azacyclohexyl) ketal (305 mg, 0.453 mmol) and triethylamine (115 mg, 0.158 ml, 1.13 mmol) in methylene chloride (10 ml) under nitrogen at room temperature was added butanesulfonyl chloride (85.2 mg, 0.070 ml, 0.544 mmol) dropwise over one minute. The mixture was stirred one hour, diluted with methylene chloride, washed with dilute potassium carbonate and brine, dried over sodium sulfate, filtered, and evaporated. The residue was purified by flash chromatography (40 g silica, 0.5% concentrated ammonium hydroxide in 5% methanol/methylene chloride) to give the title compound (216.1 mg, 60.2% yield), mass spectrum 792.4.

Method K
Descladinose azithromycin-3,6-(4-ethanesulfonyl-4-azacyclohexyl) ketal

To a solution of descladinose azithromycin-3,6-(4-azacyclohexyl) ketal (302 mg, 0.45 mmol) and diisopropylethylamine (145 mg, 0.196 ml, 1.125 mmol) in methylene chloride (10 ml) under nitrogen at −78° C. was added ethanesulfonyl chloride (69.4 mg, 0.051 ml, 0.54 mmol) in two portions. The mixture was stirred ten minutes at −78° C. and allowed to warm to room temperature. After an additional hour of stirring, the mixture was diluted with methylene chloride, washed with dilute potassium carbonate and brine, dried over sodium sulfate, filtered, and evaporated. The residue was purified by flash chromatography (40 g silica, 0.5% concentrated ammonium hydroxide in 5% methanol/methylene chloride) to give the title compound (231 mg, 67% yield), mass spectrum 764.4.

Method L
N-Desmethyl-descladinose azithromycin-3,6-(4-cyclopropylcarbonyl-4-azacyclohexyl) ketal To a solution of N-desmethyl desciadinose azithromycin-3,6-(4-azacyclohexyl)ketal (295 mg, 0.449 mmol) in dry methylene chloride (10 ml) under nitrogen at room temperature was added cyclopropanecarboxylic acid (77.3 mg, 0.898 mmol), triethylamine (136 mg, 0.188 ml, 1.35 mmol), 1-hydroxybenzotriazole hydrate (66.8 mg, 0.494 mmol) and 1-ethyl-3-(3-dimethylaminopropyl) carboduimide hydrochloride (94.7 mg, 0.494 mmol). More methylene chloride (20 ml) was added to bring the reaction mixture into solution. After stirring 2 hours, the mixture was washed with dilute potassium carbonate and brine, dried over sodium sulfate, filtered, and evaporated. The residue was purified on a chromatotron (2 mm plate), eluting with 7:1:0.1 methylene chloride/methanol/concentrated ammonium hydroxide to give the title compound (270 mg, 82.8% yield, mass spectrum 726.5).

Method M
Descladinose azithromycin-3,6-(4-(2-chloroethoxycarbonyl)-4-azacyclohexyl) ketal To a solution of descladinose azithromycin-3,6-(4-azacyclohexyl) ketal (333.3 mg, 0.496 mmol) in methylene chloride (10 ml) under nitrogen at room temperature was added diisopropylethylamine (128 mg, 0.173 ml, 0.992 mmol) and 2-chloroethyl chloroformate (63.8 mg, 0.046 ml, 0.446 mmol), The mixture was stirred 16 hours at room temperature, dilute with methylene chloride, washed with dilute potassium carbonate and brine, dried over sodium sulfate, filtered, and evaporated. The residue was purified by flash chromatography (40 g silica, 0.5% ammonium hydroxide in 5% methanol/methylene chloride) to give the title compound (255 mg, 0.328 mmol, 73% yield), mass spectrum 778.3.

Method N
N-Desmethyl-descladinose azithromycin-3,6-(4-allyloxycarbonyl-4-azacyclohexyl) ketal To a solution of N-desmethyl-descladinose azithromycin-3,6-(4-azacyclohexyl) ketal (292 mg, 0.444 mmol) in methylene chloride ( 10 ml) under nitrogen at room temperature was added triethylamine (89.8 mg, 0.124 ml, 0.888 mmol) and allylchloroformate (53.5 mg, 0.047 ml, 0.444 mmol). The mixture was stirred 3 hours at room temperature, diluted with methylene chloride, washed with dilute potassium carbonate and brine, dried over sodium sulfate, filtered, and evaporated. The residue was purified by flash chromatography (40 g silica, 0.5% ammonium hydroxide in 5% methanol/methylene chloride) to give the title compound (234 mg, 0.316 mmol, 71% yield), mass spectrum 742.3.

Method O

Descladinose azithromycin-3,6-(4-methoxycarbonyl-4-azacyclohexyl) ketal

To a solution of descladinose azithromycin-3,6-(4-azacyclohexyl) ketal (1.67 g, 2.48 mmol) and 4-dimethylaminopyridine (304 mg, 2.48 mmol) in methylene chloride (12.4 ml) at 0° C. under nitrogen was added methyl chloroformate (93.5 mg, 0.08 ml, 0.99 mmol). The mixture was stirred one hour and quenched with saturated sodium bicarbonate. The organic phase was washed with sodium bicarbonate solution and brine, dried over sodium sulfate, filtered, and evaporated. The residue was purified by flash chromatography (100 g silica, 10% methanol/methylene chloride gradient to 15% methanol/methylene chloride, impure fractions re-purified on 9.7 g silica with 1.7% ammonium hydroxide in 16/7/75 acetone/2-propanol/cyclohexane) to give the title compound (383 mg, 0.525 mmol, 53% yield), mass spectrum 730.7.

Method P

N-Desmethyl descladinose azithromycin-3,6-(4-methoxycarbonyl-4-azacyclohexyl) ketal To N-desmethyl-descladinose azithromycin-3,6-(4-azacyclohexyl) ketal (300 mg, 0.456 mmol) in a reaction vial was added dry methylene chloride (3 ml) and potassium carbonate 600 mg, 4.35 mmol) which had been ground and dried in a microwave oven. Methyl chloroformate (51.7 mg, 0.042 ml, 0.547 mmol) was added via syringe, and the mixture stirred at room temperature 16 hours. The reaction mixture was washed twice with brine, dried over sodium sulfate, and purified on a chromatotron (2mm plate) using 10/1/0.1 methylene chloride/methanol/ammonium hydroxide, to give the title compound (204 mg, 0.284 mmol, 62% yield), mass spectrum 716.4.

Method Q

Descladinose azithromcin-3,6-(4-alllyurea-4-azacyclohexyl) ketal

To descladinose azithromycin-3,6-(4-azacyclohexyl) ketal (200 mg, 0.3 mmol) in anhydrous methylene chloride (2.5 ml) at room temperature under nitrogen was added allyl isocyanate (30 mg, 0.032 ml, 0.362 mmol). The mixture was stirred two hours, diluted with methylene chloride, washed with saturated sodium bicarbonate and brine, dried over sodium sulfate, filtered, and evaporated. The residue was purified by flash chromatography (10 g silica, 1% ammonium hydroxide in 5% methanol/methylene chloride) to give the title compound (113 mg, 0.149 mmol, 41% yield), mass spectrum 755.5.

Method R

Descladinose azithromycin-3,6-(4-acetoxyacetyl-4-azacyclohexyl) ketal

To descladinose azithromycin-3,6-(4-azacyclohexyl) ketal (200 mg, 0.3 mmol) in methylene chloride (5 ml) at room temperature under nitrogen was added pyridine (19.6 mg, 0.020 ml, 0.25 mmol) and acetoxyacetyl chloride (50.8 mg, 0.04 ml, 0.372 mmol). The mixture was stirred one hour, diluted with methylene chloride, washed with saturated sodium bicarbonate and brine, dried over sodium sulfate, filtered, and evaporated. The residue was stirred in methanol (2 ml) one hour and evaporated. The residue was purified by flash chromatography (10 g silica, 2% ammonium hydroxide in 10% methanol/methylene chloride) to give the title compound (96.8 mg, 0.125 mmol, 41.7% yield), mass spectrum 772.4.

Method S

Descladinose azithromycin-3,6-(4-cyclopropylcarbonyl-4-azacyclohexyl) ketal

To descladinose azithromycin-3,6-(4-azacyclohexyl) ketal (200 mg, 0.3 mmol) in methylene chloride (2.5 ml) at room temperature under nitrogen was added pyridine (19.6 mg, 0.020 ml, 0.25 mmol) and cyclopropanecarbonyl chloride (12.7 mg, 0.011 ml, 0.121 mmol). The mixture was stirred one hour, and methanol (1.3 ml) was added. The reaction was stirred an additional three hours, evaporated, taken up in methylene chloride, washed with saturated sodium bicarbonate and brine, dried over sodium sulfate, filtered, and evaporated. The residue was purified by flash chromatography (10 g silica, 1% ammonium hydroxide in 5% methanol/methylene chloride) to give the title compound (135.7 mg, 0.183 mmol, 61% yield), 15 mass spectrum 740.5.

Method T

Descladinose azithromycin-3,6-(4-hydroxyacetyl-4-azacyclohexyl) ketal

To descladinose azithromycin-3,6-(4-acetoxyacetyl-4-azacyclohexyl) ketal (20 mg, 0.026 mmol) in methanol (1 ml) was added potassium carbonate (2 mg, 0.014 mmol). The mixture was stirred 16 hours at room temperature and evaporated to give the title compound as a mixture with residual potassium salts (13.8 mg total weight), mass spectrum 730.6.

Method U

Descladinose azithromycin-3,6-(4-cyclopropyl-4-azacyclohexyl) ketal

To descladinose azithromycin-3,6-(4-azacyclohexyl) ketal (168 mg, 0.25 mmol) in methanol (5 ml) was added [1-ethoxycyclopropyl)oxy]trimethylsilane (218 mg, 0.25 ml, 1.25 mmol), sodium cyanoborohydride (63 mg, 1 mmol), acetic acid (150 mg, 0.143 ml, 2.5 mmol) and 3A molecular sieves (150 mg). The mixture was heated to reflux under nitrogen for ten hours, filtered, concentrated, and diluted with methylene chloride and saturated sodium bicarbonate. The organic layer was separated, and the aqueous layer extracted with methylene chloride. The combined organic layers were washed with saturated sodium bicarbonate and brine, dried over sodium sulfate, filtered, and evaporated. The residue was purified by flash chromatography (5 g silica, 0.4% ammonium hydroxide in 5% methanol/methylene chloride, gradient to 0.4% ammonium hydroxide in 6% methanol/methylene chloride) to give the title compound (56 mg, 0.079 mmol, 31.5% yield), mass spectrum 712.4.

Method V

Descladinose azithromycin-3,6-benzaldehyde acetal

To descladinose azithromycin (3 g, 5.08 mmol) in benzene (125 ml) was added benzaldehyde dimethyl acetal (7.7 g, 7.6 ml, 50.76 mmol) and p-toluenesulfonic acid monohydrate (20 mg). The reaction mixture was heated to reflux under a Dean-Stark trap for 24 hours, and additional benzaldehyde dimethyl acetal was added (15.4 g, 15.2 ml, 0.101 mol). Refluxing was continued for two more days, the benzene was removed under reduced pressure, and most of the excess benzaldehyde dimethyl acetal distilled off under vacuum. The residual oil was purified by successive silica gel flash chromatography, eluting with 0.2% ammonium hydroxide in 1% methanol/chloroform, to give the two diastereomers of the title compound (707 mg and 408 mg, total 1.64 mmol, 32% yield, absolute configurations not assigned), mass spectrum 679.6.

Method W
Descladinose-9-dihydroerythromycin-3,6-(4-methyl-4-azacyclohexyl) ketal To a suspension of descladinose-9-dihydroerythromycin-3,6-(4-azacyclohexyl) ketal (250 mg, 0.379 mmol) in water (5 ml) was added formaldehyde (37% solution in water, 0.12 ml, 47.9 mg as formaldehyde, 1.6 mmol) and formic acid (0.57 ml, 695 mg, 15.1 mmol). The solution was heated to reflux for five hours, and stirred at room temperature for an additional 20 hours. The mixture was poured into saturated sodium bicarbonate solution and extracted three times with ethyl acetate. The combined organic extracts were washed with brine, dried over sodium sulfate, filtered, and evaporated to give the title compound (120 mg, 0.188 mmol, 50% yield), mass spectrum 637.4.

Method X
4"-Isopropenyloxy-Azithromycin

To a solution of azithromycin (130 mg, 0.17 mmol) in methylene chloride (10 ml) was added 2-methoxypropene (0.5 ml, 376.5 mg, 5.22 mmol) and pyridinium hydrochloride (60 mg, 0.52 mmol). The solution was stirred under nitrogen at room temperature two days, washed with saturated sodium bicarbonate and brine, filtered through cotton wool, and concentrated. The residue was purified by flash chromatography (10 g silica, 95:5:1 methylene chloride/methanol/ammonium hydroxide) to give the title compound (124 mg, 0.157 mmol, 92% yield), mass spectrum 789.

Method Y
4"-Isopropenvioxy-N-desmethylazithromycin

To a solution of N-desmethylazithromycin (538.4 mg, 0.732 mmol) in methylene chloride (10 ml) in an ice bath under nitrogen was added 4Å molecular sieves (20), 2-methoxypropene (2 ml, 1.5 g, 20.9 mmol) and pyridinium hydrochloride (171 mg, 1.48 mmol). The mixture was allowed to warm to room temperature and stirred 18 hours. Additional 2-methoxypropene (3 ml, 2.25 g, 31.2 mmol) and pyridinium hydrochloride (145 mg, 1.25 mmol) were added. After stirring an additional 23 hours at room temperature, the reaction mixture was diluted with methylene chloride, washed with saturated sodium bicarbonate, dried over sodium sulfate, and concentrated. The residue was purified by flash chromatography (20 g silica, step gradient-0.1% ammonium hydroxide in 2.5% methanol/methylene chloride; 0.1% ammonium hydroxide in 4% methanol/methylene chloride; 0.1% ammonium hydroxide in 10% methanol/methylene chloride) to give the title compound (482 mg, 0.623 mmol, 85% yield), mass spectrum 774.

Method Z
N-Desmethylazithromycin-4"-(1-cyclohexenyl) ether

To a solution of N-desmethylazithromycin (648 mg, 0.88 mmol) in methylene chloride (50 ml) was added 1-methoxycyclohexene (6.03 g, 52.9 mmol) and pyridinium p-toluenesulfonate (1.33 g, 5.28 mmol). The mixture was stirred under nitrogen at room temperature for 5 days, diluted with methylene chloride, washed with dilute sodium bicarbonate and brine, dried over sodium sulfate, filtered, and evaporated. The residue was purified by flash chromatography (60 g silica, 0.1% ammonium hydroxide in 7% methanol/methylene chloride) to give the title compound (235 mg, 32.8% yield), mass spectrum 816.

Method AA
N-Desmethylazithromycin -4"-(1-cyclopentenyl) ether

To a solution of N-desmethylazithromycin (735 mg, 1 mmol) in methylene chloride (50 ml) was added 1-methoxycyclopentene (5.88 g, 60 mmol) and pyridinium p-toluenesulfonate (1.33 g, 6 mmol) and p-toluenesulfonic acid (360 mg, 1.9 mmol). The mixture was stirred seven days, diluted with methylene chloride, washed with dilute potassium carbonate and brine, dried over sodium sulfate, filtered, and evaporated. The residue was purified by flash chromatography (60 g silica, 0.8% ammonium hydroxide in 8% methanollmethylene chloride) to give the title compound (232 mg, 0.29 mmol, 29% yield), mass spectrum 802.

Method AB
Addition of Arylalkyl Groups to 3,6-Azacycloalkyl Ketals

To N-desmethyl-descladinose azithromycin-3,6-(4-azacyclohexyl) ketal (250 mg to 500 mg) or descladinose azithromycin-3,6-(4-azacyclohexyl) ketal (250 mg to 500 mg) in $CH_2Cl_2$ was added substituted benzyl bromide or substituted benzyl chloride (1.2 to 2 eq) and $Et_3N$ (3 eq) at room temperature. The reaction mixture was stirred for 24–48 hours and quenched with saturated sodium bicarbonate solution. The organic layer was washed with saturated sodium bicarbonate solution and brine, dried over sodium sulfate, filtered and organic solvent removed in vacuo. The residue was purified by flash chromatography using 3–6% $MeOH/CHCl_3$, 0.5% ammonia to give the corresponding compound in which the nitrogen of the 4-azacyclohexyl moiety was substituted with the substituted benzyl group. When N-desmethyl-descladinose azithromycin-3,6-(4-azacyclohexyl) ketal was used, the disubstituted benzyl derivative (ring N-9a was also benzylated) was also isolated as a minor product.

Method AC
Procedure For Reductive Amination 3,6-Azacycloalkyl Ketals

To N-desmethyl-descladinose azithromycin-3,6-(4-azacyclohexyl) ketal (250 mg to 500 mg) or descladinose azithromycin-3,6-(4-azacyclohexyl)ketal (250 mg to 500 mg) in $CH_2Cl_2$, an aldehyde of the formula RC(O)H wherein R corresponds to the various carbonyl moieties provided in the definition of $R^6$, referred to above, and specifically referred to in the tables of examples below (2.5 eq.), and sodium sulfate (10 eq.) or molecular sieves (3Å) were mixed in a round bottom flask and dried under vacuum. $CH_2Cl_2$ (10–20 mL) was added to the flask, followed by the addition of acetic acid (3 eq.), and the mixture was stirred at room temperature for 15 minutes. NaB(OAc)3H (2 eq.) was then added, and the stirring was continued at room temperature for 2 to 14 hours. The reaction was then quenched with saturated sodium bicarbonate solution, and the product was extracted with $CH_2Cl_2$ (3×50 mL). The combined organic layers were washed with brine, and dried with sodium sulfate, and organic solvent was removed in vacuo to give the crude product which was purified by flash chromatography using 3–5% $MeOH/CHCl_3$ and 0.5% concentrated ammonia.

Method AD
Procedure For Coupling Ketals With Aromatic Acids

N-desmethyl-descladinose azithromycin-3,6-(4-azacyclohexyl) ketal (250 mg to 500 mg) or descladinose azithromycin-3,6-(4-azacyclohexyl) ketal (250 mg to 500 mg), an acid of the formula RC(O)OH wherein R is defined as provided in Method AC (2 eq.), EDC (1.2 eq.), HOBT (1.2 eq.) were mixed and dried under vacuum. After the mixture was dissolved in $CH_2Cl_2$ (10 mL), $Et_3N$ (4 eq.) was added, and the resulting solution was stirred at room temperature for 24 to 48 hours. The reaction was then quenched with saturated sodium bicarbonate solution, and the product was extracted with $CH_2Cl_2$ (3×50 mL). The combined organic layers were washed with brine, and dried with sodium sulfate, and organic solvent was removed in vacuo to give the crude product which was purified by flash chromatography using 3–5% $MeOH/CHCl_3$ and 0.5% concentrated ammonia.

Method AE
Descladinose azithromycin-3,6-(4-(1-propen-3-yl)-4-azacyclohexyl)ketal Descladinose azithromycin-3,6-(4-azacyclohexyl)ketal (250 mg, 0.372 mmol) was dissolved in toluene (5 mL), followed by the addition of $Et_3N$ (259 μL, 1.86 mmol), $Pd(PPh_3)_4$ (43.0 mg, 0.0372 mmol), allyl acetate (48.0 μL, 0.446 mmol). The reaction mixture was stirred at 80° C. overnight, and TLC showed the reaction was complete. The reaction solution was taken into EtOAc, washed with saturated $NaHCO_3$ solution, water, and brine. The solvent was then removed in vacuo to give the crude product which was purified by flash chromatography using 6% methanol, 0.2% ammonia in chloroform to give the desired product (215 mg, 81% yield).

Method AF
N-desmethyl-descladinose azithromycin-3,6-(4-(5-nitropyridin-2-yl)-4-40 azacyclohexyl)ketal A mixture of N-desmethyl-decladinose azithromycin-3,6-(4-azacyclohexyl)ketal (200 mg, 0.30 mmol) and 2-chloro-5-nitro pyridine (73 mg, 1.5 equiv) in dry acetonitrile (1.4 ml) was treated with triethylamine (46 mg, 1.5 equiv) and the resulting mixture was refluxed 2 hours until completion of the reaction. The solvent was removed in vacuo and the crude mixture was purified by flash chromatography with 0–5% $Et_2NH/EtOAc$ to provide the desired product (214.6 mg, 90%) as a pale yellow solid.

Method AG
N-desmethyl-descladinose azithromycin-3,6-(4-diphenylphosphinyl-4-azacyclohexyl)ketal Descladinose azithromycin-3,6-(4-azacyclohexyl)ketal was dissolved in methylene chloride, and the resulting solution was stirred in an ice-water bath. Phosphinic chloride was added dropwise to the reaction flask, and the reaction was followed by TLC. After the reaction was finished, the reaction mixture was diluted with $CH_2Cl_2$, the organic layer was washed with saturated sodium bicarbonate solution, water, and brine. The organic layer was dried with sodium sulfate, and the solvent was removed in vacuo to give the crude product which was purified by flash chromatography.

Method AH
N-desmethyl-descladinose azithromycin-3,6-(4-(2-fluoro-4-benzyloxycarbonyl-phenyl)-4-azacyclohexyl)ketal N-desmethyl-decladinose azithromycin-3,6-(4-azacyclohexyl)ketal (329 mg, 0.500 mmol) and benzyl 3,4-difluorobenzoate were dissolved in isopropanol (2 mL), followed by the addition of N,N-diisopropylethylamine (193 mg, 1.50 mmol). The reaction mixture was then heated at 85° C. and followed by TLC. After 12 hours stirring, the reaction mixture was taken into methylene chloride (100 mL), and washed with brine (100 mL). The organic layer was dried with sodium sulfate, and the solvent was removed in vacuo to give the crude product which was purified by preparative TLC plate using 10% MeOH, 1% ammonia in methylene chloride to give the title compound (26 mg, 6% yield).

Method AI
N-desmethyl-descladinose azithromycin-3,6-(4-(2-fluoro-4-(4-pyridylmethylaminocarbonyl)-phenyl)-4-azacyclohexyl)ketal N-desmethyl-descladinose azithromycin-3,6-(4-azacyclohexyl)ketal (300 mg, 0.446 mmol) and 4'-pyridylmethyl-3,4-difluorobenzoate were dissolved in DMF (2 mL), followed by the addition of N,N-diisopropylethylamine (173 mg, 1.34 mmol). The reaction mixture was then heated at 95° C. and followed by TLC. After 48 hours stirring, the reaction mixture was taken into methylene chloride (100 mL), and washed with brine (100 mL). The organic layer was dried with sodium sulfate, and the solvent was removed in vacuo to give the crude product which was purified by preparative TLC plate using 10% MeOH, 0.5% ammonia in methylene chloride to give the title compound (8 mg, 2% yield).

Method AK
N-desmethyl-N-benzyl-descladinose azithromycin-3,6-(4-(2-pvrazinvIcarbonyl)-4-azacyclohexyl)ketal N-desmethyl-descladinose azithromycin-3,6-(4-2'-pyrazinylcarbonyl-4-azacyclohexyl)-ketal (100 mg, 0.131 mmol) and benzyl bromide (31.0 μL, 0.262 mmol) were dissolved in dioxane (1 ml), followed by the addition of $Et_3N$ (55 μL, 0.393 mmol). After the reaction solution was stirred at room temperature for 12 hours, it was taken into $CH_2Cl_2$, and the organic layer was washed with saturated sodium bicarbonate solution. The organic layer was dried ($Na_2SO_4$), and solvent was removed in vacuo to give the crude product which was purified by flash chromatography using 6% MeOH, 0.5% ammonia in methylene chloride to give the title compound (8 mg, 7% yield).

Method AL
N-desmethyl-N-p-methoxybenzyl-descladinose azithromycin-3,6-(4-(pyrazinylcarbonyl)-4-azacyclohexyl)ketal N-desmethyl-descladinose azithromycin-3,6-(4-2'-pyrazinylcarbonyl)-4-azacyclohexyl)-ketal (100 mg, 0.131 mmol) and p-methoxy-benzyl chloride (36.0 μL, 0.262 mmol) were dissolved in dioxane (1 ml), followed by the addition of $Et_3N$ (55 μL, 0.393 mmol). After the reaction solution was stirred at room temperature for 12 hours, it was taken into $CH_2Cl_2$, and the organic layer was washed with saturated sodium bicarbonate solution. The organic layer was dried ($Na_2SO_4$), and solvent was removed in vacuo to give the crude product which was purified by flash chromatography using 6% MeOH, 0.5% ammonia in methylene chloride to give the title compound (37.0 mg, 32% yield).

Method AM
N-desmethyl-descladinose azithromycin-3,6-(4-(2-benzyloxime)-propanoyl-4-azacyclohexyl)ketal N-desmethyl-descladinose azithromycin-3,6-(4-pyruvyl-4-azacyclohexyl)ketal (150 mg, 0.206 mmol) and O-benzylhydroxylamine hydrochloride (165 mg, 1.03 mmol) were mixed in a vial equipped with a septum cap, followed by the addition of pyridine (1 mL). The vial was placed on a shaker, and the shaker was shaken at 60° C. overnight. The reaction mixture was taken into methylene chloride, and washed with saturated $NaHCO_3$ solution, then brine. The organic layer was dried, and the solvent was removed in vacuo to give the title product in quantitative yield.

Method AN
N-desmethyl-descladinose azithromycin-3,6-(4-(2-pentafluorobenzyloxime)propanoyl-4-azacyclohexyl)ketal N-desmethyl-descladinose azithromycin-3,6-(4-pyruvyl-4-azacyclohexyl)ketal (150 mg, 0.206 mmol) and O-pentafluorobenzylhydroxylamine hydrochloride (165 mg, 1.03 mmol) were mixed in a vial equipped with a septum cap, followed by the addition of pyridine (1mL). The vial was placed on a shaker, and the shaker was shaken at 60° C. overnight. The reaction mixture was taken into methylene chloride, and washed with saturated $NaHCO_3$ solution, then brine. The organic layer was dried, and the solvent was removed in vacuo to give the product in quantitative yield.

Method AO

N-desmethyl-descladinose azithromycin-3,6-(4-(2,2-di-(ethoxycarbonyl)-ethen-1-yl)-4-azacyclohexyl)ketal A solution of N-desmethyl-descladinose azithromycin-3, 6-(4-azacyclohexyl)ketal (250 mg, 0.38 mmol) in dichloromethane under nitrogen was treated with the enone diethyl ethoxymethylene malonate (0.12 ml, 0.57 mmol) in one portion. The mixture was stirred at room temperature overnight, until the reaction was completed. The solvent was evaporated in vacuo and the resulting crude mixture was purified by flash column chromatography (45 g silica, 95:5:1 methylene chloride/methanol/ammonium hydroxide) to provide the desired product CP-547089 (37.9 mg) as a pale yellow solid.

Method AP

N-desmethyl-descladinose azithromycin-3,6-(4-(4-carbobenzyloxy-3-trifluoromethyl)phenyl-4-azacyclohexyl)ketal To a solution of N-desmethyl-descladinose azithromycin-3,6-(4-azacyclohexyl) ketal (1.47 g, 2.23 mmol) and potassium carbonate (308 mg, 2.23 mmol) in acetonitrile (22 mL) was added benzyl 4-fluoro-2-(triflouromethyl)benzoate (2.00 g, 6.71 mmol). The flask was fitted with a reflux condenser and heated to 82° C. for 7 days. After cooling to room temperature the solution was diluted with methylene chloride and filtered through celite. The filtrate was concentrated and the residue was purified by flash chromatography (silica gel, 0.2% ammonium hydroxide (10% aqueous) in 10% methanol/methylene chloride to give the title compound (470 mg, 23% yield), mass spectrum 937 (M+1).

Method AQ

Descladinose azithromycin-3,6-(4-(thiazo-2-yl)-4-azacyclohexyl)ketal

To a solution of descladinose azithromycin-3,6-(4-azacyclohexyl) ketal (100 mg, 0.15 mmol) and diisopropylethylamine (0.036 mL, 0.21 mmol) in 2-propanol (1.5 mL) was added 2-chlorothiazole (0.014 mL, 0.16 mmol). The flask was fitted with a reflux condenser and heated to 80° C. for 24 hours. After cooling to room temperature the mixture was transferred to a separatory funnel and diluted with methylene chloride (20 mL). The mixture was washed with water (10 mL). The layers were separated and the aqueous fraction was extracted with methylene chloride (2×5 mL). The combined methylene chloride fractions were dried over sodium sulfate, filtered, and concentrated. The residue was purified by flash chromatography (silica gel, 0.2% ammonium hydroxide (10% aqueous) in 10% methanol/methylene chloride to give the title compound (54.6 mg, 48% yield), mass spectrum 756 (M+1).

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention in the treatment of a bacterial, parasitic or protozoal infection, or a disorder related to a bacterial, parasitic or protozoal infection, may be assessed by subjecting the claimed compounds to one or more of the following assays.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermAlermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant, The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/ml to 0.098 µg/ml by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/ml. The MIC is equal to the concentration of the test compound exhibiting 100% inhibition of growth of *P. haemolytica* as determined by comparison with an uninoculated control.

The in vivo activity of the compounds of the present invention can be determined by conventional animal protection studies well known to those skilled in the art, usually carried out in rodents.

Assay IV

Murine *P. Multocida* Infection Model

Mice are allotted to cages upon their arrival, and allowed to acclimate before being used. Animals are inoculated with a bacterial suspension (P. multocida strain 59A006) intraperitoneally. Each experiment has at least 3 non-medicated control groups including one infected with 0.1× challenge dose and two infected with 1X challenge dose; a 1OX challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. Subcutaneous doses are administered into the loose skin in the back of the neck whereas oral doses are given by means of a feeding needle. In both cases, a volume of 0.2 ml is used per mouse. A control compound of known efficacy administered by the same route is included in each test. Animals are observed daily, and the number of survivors in each group is recorded for 72 hours (three days) post challenge. The PD50 is a calculated dose at which the compound tested protects 50% of a group of mice from mortality due to the bacterial infection which would be lethal in the absence of drug treatment.

Assay V

Murine *Staohyiococcus aureus* Intraperitoneal Infection Model

Mice (female CF-1) are allotted to cages (10 per cage) upon their arrival, and allowed to acclimate for a minimum of 48 hours before being used. Mice are infected intraperitoneally with 0.5 ml of a 3 to 5×10⁵ colony forming units (CFU)/ml log phase culture of *Staphylococcus aureus* strain UC 6097 in 5% hog gastric mucin. Each experiment has one infected, non-medicated control group. Generally, all mice in a given study can be challenged within 30 to 90 minutes, especially if a repeating syringe (such as a Cornwall® syringe) is used to administer the challenge culture. Thirty minutes after infection has begun, compound treatment is given. It may be necessary for a second person to begin compound dosing if all of the animals have not been challenged at the end of thirty minutes. Subcutaneous doses are administered into the loose skin in the back of the neck whereas oral doses are given by means of a feeding needle. In both cases, a volume of 0.2 ml is used per mouse. A control compound of known efficacy administered by the same route is included in each test. Animals are observed daily, and the number of survivors in each group is recorded for 72 hours (three days) post challenge. The PD50 is a calculated dose at which the compound tested protects 50% of a group of mice from mortality due to the bacterial infection which would be lethal in the absence of drug treatment.

Assay VI

Murine *Staphylococcus aureus* Intramammary Infection Model

Lactating mice (female CF-1 that gave birth 2 to 5 days prior to the day of infection) (female CF-1) are allotted to cages (1 per cage) upon their arrival, and allowed to acclimate for 24–48 hours before being used. Mice are infected in the L4 mammary gland with 0.1 ml of a 300 to 450 colony forming units (CFU)/ml log phase culture of *Staphylococcus aureus* strain UC 6097. Each experiment has one infected, non-medicated control group. Thirty minutes after infection has begun, compound treatment is given. Subcutaneous doses are administered into the loose skin in the back of the neck whereas oral doses are given by means of a feeding needle. In both cases, a volume of 0.2 ml is used per mouse. The endpoint is the presence or absence of clinical mastitis symptoms and quantitation of bacterial numbers in the mammary glands five days after infection. Bacteria are quantitated by homogenizing the infected gland with 4 volumes of phosphate buffered saline for 30 seconds (Omni International, model TH). The homogenate and dilutions of the homogenate are plated on Brain Heart Infusion Agar, incubated at 37° C. overnight, and the colonies counted. The lower limit of detection is 50 CFU/gland. Infected, non-medicated mice have ~5×10⁹ CFU/gland at the time of necropsy.

Assay VII

Determination Of MIC Of *Fusobacterium necrophorum* Isolated Using Anaerobic Plate Dilution Techniques Minimum inhibitory concentration (MIC) data may be collected from isolates of *Fusobacterium necrophorum* of cattle and sheep origin. The MIC values for *Fusobacterium necrophorum* are determined using plate dilution techniques and inoculation with a Steer's replicator. The procedures are those outlined in "Methods For Antimicrobial Susceptibility Testing Of Anaerobic Bacteria-Third Edition; Approved Standard" (vol. 13, no. 26, 1993) by the National Committee on Clinical Laboratory Standards (NCCLS). A total of 10 dilutions of the antimicrobials are tested as doubling dilutions of the drug (32 to 0.063 mcg/ml). Control strains of anaerobic bacteria (*Clostridium perfringens* ATCC 13124 and *Bacteroides fragilis* ATCC 25285) are used as controls on each inoculated plate.

The compounds of the present invention, and the pharmaceutically acceptable salts thereof (hereinafter "the active compounds"), may be adminstered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed.

Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

In the treatment of cancer, in particular non-small cell lung cancer, the active compounds may be administered as described in European patent application publication number 758,549, published Feb. 2, 1997.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 99% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

In Tables 1 and 2 below, "Ex." refers to the Example number; "T" refers to the template structure appearing before the table; "P" refers to the specific method used to prepare the 35 example as described above in Methods A–AP; HPLC I, II, and III refer to the HPLC data associated with the example; and "Mass Spec" refers to the mass spectrometry data associated with the example. The HPLC measurements were conducted using an HP1050 (manufactured by Hewlett Packard) as the instrument with the following detector conditions: 1050 DAD 2 nm slit, ELSD tube temp 113° C. HPLC I included the following conditions: column—Prodigy 3.2×250 mm C-8; A=0.050M $NH_4OAc$+0.1% TFA freshly prepared, C=acetonitrile; gradient—80:20 A:C to 20:80 A:C over 30 minutes; flow rate—0.5 mL/minute. HPLC II included the following conditions: column—YMC 4.6×250 mm C-8; 70% 0.050M $NH_4OAc$, 30% acetonitrile; flow rate—1 mL/minute. HPLC III included the following conditions: column—YMC 4.6× 250 mm C-8; 65% 0.050M $NH_4OAc$, 35% acetonitrile; flow rate—1 mL/minute.

Templates For Tables

T-1
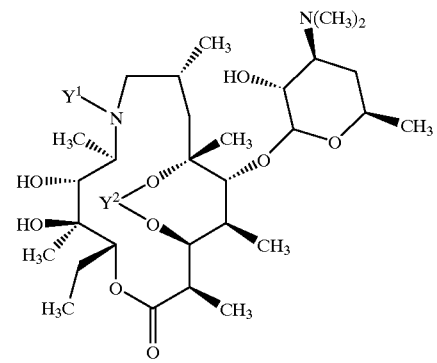

T-2
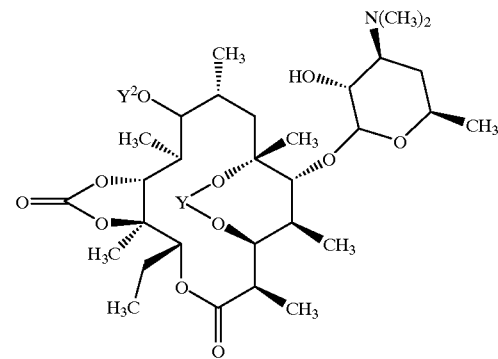

T-3
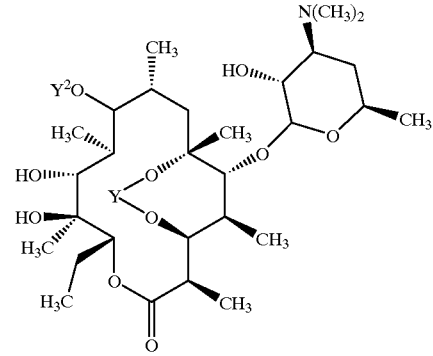

33
-continued
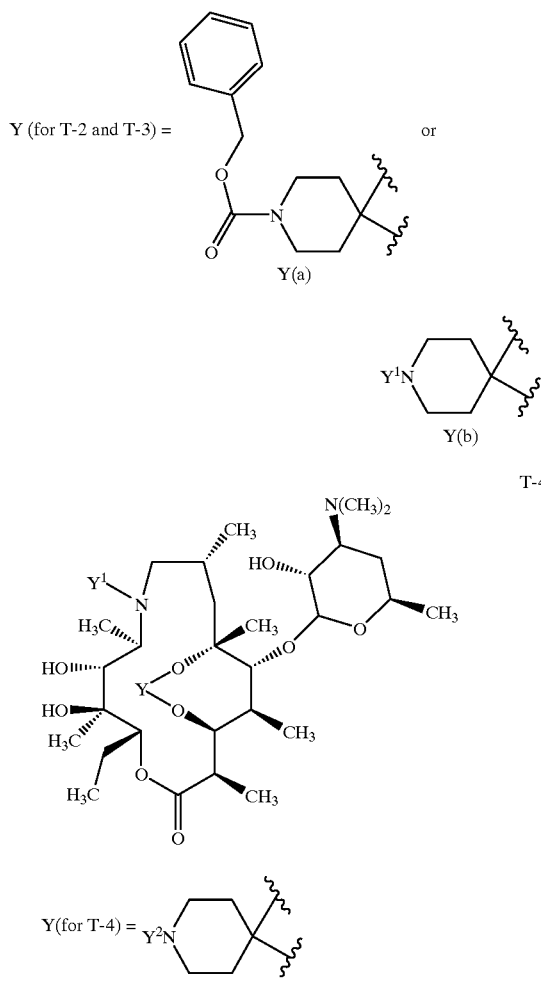
34
-continued
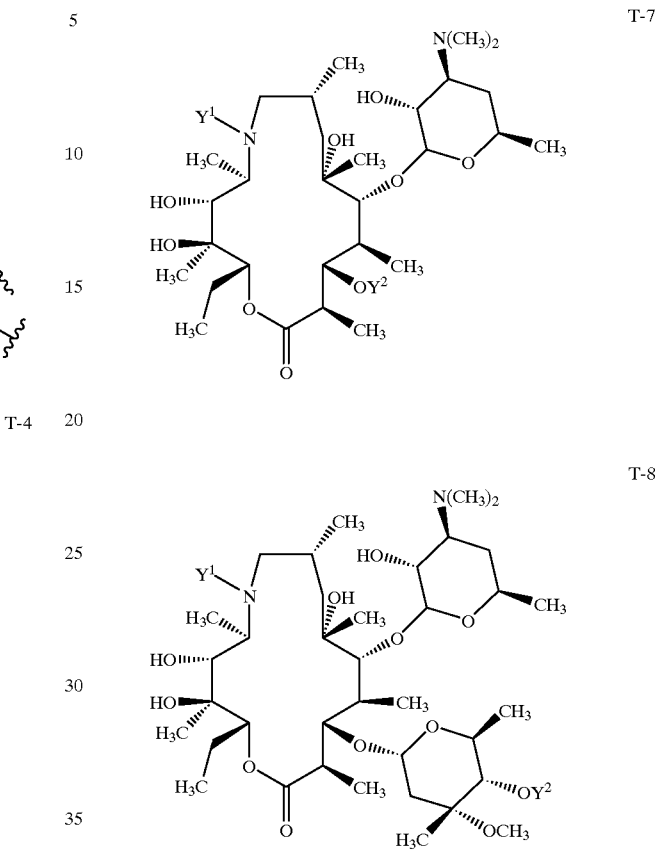
TABLE 1
| Ex. | T | $Y^1$ | $Y^2$ | P | HPLC I | HPLC II | HPLC III | Mass Spec. |
|---|---|---|---|---|---|---|---|---|
| 1 | T-1 | $CH_3$ | $\begin{array}{c}H_3C\\ \phantom{x}\diagup\phantom{x}\\ H_3C\end{array}$ | A | | | 26.43 | 632 |
| 2 | T-1 | $CH_3$ | cyclohexyl | A | | | 75.00 | 672 |
| 3 | T-1 | H | cyclopentyl | A | | | 17.92 | 643 |

TABLE 1-continued
| Ex. | T | Y¹ | Y² | P | HPLC I | HPLC II | HPLC III | Mass Spec. |
|---|---|---|---|---|---|---|---|---|
| 4 | T-1 | H | 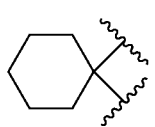 | A | | | >60 | 657 |
| 5 | T-1 | H | 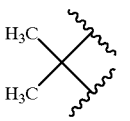 | A | | 10.8 | | 617 |
| 6 | T-1 | H | 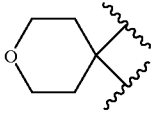 | B | 10.91 | | | 658.7 |
| 7 | T-4 | H | —C(O)O(benzyl) | D | | 3.28 | | 792.4 |
| 8 | T-4 | H | H | G | 4.09 | 3.13 | | 658.4 |
| 9 | T-4 | CH₃ | H | G | 3.62 | 3.74 | | 672.4 |
| 10 | T-4 | CH₃ | —C(O)O(benzyl) | D | 16.76 | | | 806.5 |
| 11 | T-4 | H | —C(O)CH₃ | F | | 5.71 | | 700.6 |
| 12 | T-4 | CH₃ | CH₃ | H | | 3.71 | | 686.6 |
| 13 | T-1 | H | 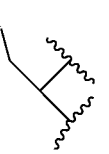 | U | | | | 637.4 |
| 14 | T-1 | CH₃ | 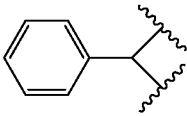 | V | 18.98 | | | 679.6 |
| 15 | T-1 | CH₃ | 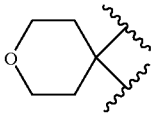 | B | 9.79 | | | 673.4 |
| 16 | T-4 | CH₃ | —C(O)CH₃ | C | | 10.14 | | 714.5 |
| 17 | T-1 | H | 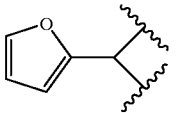 | U | | | | 655.4 |
| 18 | T-4 | CH₃ | —C(O)OCH₃ | O | | 35.35 | | 730.5 |
| 19 | T-4 | H | —C(O)OCH₂CH₃ | C | | 23.00 | | 730.5 |
| 20 | T-4 | CH₃ | —C(O)OCH₂CH₃ | C | 12.93 | | | 744.5 |
| 21 | T-4 | CH₃ | —SO₂CH₃ | I | | 24.14 | | 750.5 |
| 22 | T-1 | H | 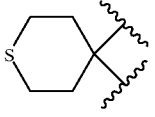 | E | 14.38 | | | 675.7 |
| 23 | T-4 | CH₃ | —C(O)NHCH(CH₃)₂ | Q | | 22.21 | | 757.7 |
| 24 | T-4 | CH₃ | —C(O)CH₂OC(O)CH₃ | R | | 13.87 | 772.4 | |

TABLE 1-continued

| Ex. | T | Y¹ | Y² | P | HPLC I | HPLC II | HPLC III | Mass Spec. |
|---|---|---|---|---|---|---|---|---|
| 25 | T-1 | $CH_3$ | 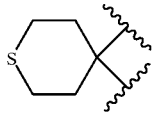 | E | 13.83 | | | 689.4 |
| 26 | T-4 | $CH_3$ | 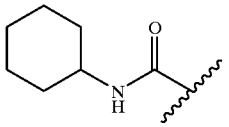 | Q | | | | 797.6 |
| 27 | T-4 | H | —C(O)OC(CH₃)₃ | C | 16.47 | | | 758.5 |
| 28 | T-4 | $CH_3$ | —C(O)OC(CH₃)₃ | C | 15.54 | | | 772.5 |
| 29 | T-2 Y(a) | — | H | B | | | | 819 |
| 30 | T-2 Y(a) | — | 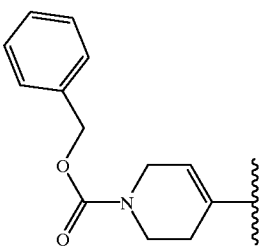 | B | | | | 1034 |
| 31 | T-3 Y(a) | — | H | B | 20.89 | | | 793.4 |
| 32 | T-3 Y(b) | H | H | G | | 3.80 | | 659.5 |
| 33 | T-3 Y(b) | $CH_3$ | H | W | 7.72 | | | 637.4 |
| 34 | T-4 | $CH_3$ | —C(O)CH₂OH | T | | 8.18 | | 730.6 |
| 35 | T-4 | $CH_3$ | —C(O)(cyclopropyl) | S | | 25.45 | | 740.5 |
| 36 | T-4 | $CH_3$ | —C(O)CH₂CH₃ | S | | 16.60 | | 728.4 |
| 37 | T-2 Y(b) | H | 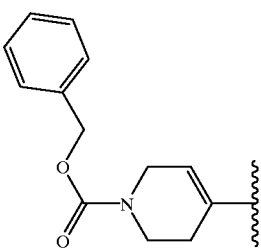 | G | | | | 900.5 |
| 38 | T-2 Y(b) | H | 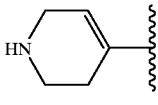 | G | | | | 766.5 |
| 39 | T-4 | $CH_3$ | —C(O)OCH₂CH=CH₂ | N | 14.16 | | | 756.4 |
| 40 | T-4 | $CH_3$ | —C(O)OCH=CH₂ | N | 17.15 | | | 742.4 |
| 41 | T-4 | $CH_3$ | —C(O)O(CH₂)₂Cl | M | 13.85 | | | 778.3 |
| 42 | T-4 | $CH_3$ | —C(O)OCH₂C(Cl)₃ | M | 21.66 | | | 845.6 |
| 43 | T-4 | $CH_3$ | —C(O)NHCH₂CH=CH₂ | Q | | 17.92 | | 755.5 |
| 44 | T-4 | $CH_3$ | —C(O)OCH₂CH(CH₃)₂ | N | 19.19 | | | 772.5 |
| 45 | T-4 | $CH_3$ | —SO₂(CH₂)₃CH₃ | J | 15.39 | | | 792.4 |
| 46 | T-4 | $CH_3$ | —C(O)NHCH₂CH₃ | Q | | | | 743.5 |
| 47 | T-4 | $CH_3$ | —SO₂CH(CH₃)₂ | K | 12.83 | | | 778.3 |
| 48 | T-4 | $CH_3$ | —SO₂CH₂CH₃ | K | | 29.13 | | 764.4 |
| 49 | T-4 | $CH_3$ | benzylsulfonyl | K | 15.31 | | | 826.4 |
| 50 | T-4 | $CH_3$ | cyclopropyl | U | | 32.79 | | 712.4 |
| 51 | T-4 | | Both Y¹ and Y² are cyclopropyl | U | | | | 738.4 |

TABLE 1-continued

| Ex. | T | Y¹ | Y² | P | HPLC I | HPLC II | HPLC III | Mass Spec. |
|---|---|---|---|---|---|---|---|---|
| 52 | T-4 | H | cyclopropyl | U | | 9.52 | | 698.3 |
| 53 | T-4 | H | —C(O)OCH$_2$CH=CH$_2$ | N | | 25.38 | | 742.3 |
| 54 | T-4 | H | —C(O)O(CH$_2$)$_2$Cl | M | 13.29 | | | 764.2 |
| 55 | T-4 | H | —C(O)(cyclopropyl) | L | | 10.32 | | 726.5 |
| 56 | T-4 | H | —C(O)CH$_2$OH | L | | 4.86 | | 716.4 |
| 57 | T-4 | H | —C(O)CH$_2$OC(O)CH$_3$ | L | | 6.99 | | 758.4 |
| 58 | T-4 | H | —C(O)OCH$_3$ | P | | 12.41 | | 716.4 |
| 59 | T-4 | H | —C(O)NHCH(CH$_3$)$_2$ | Q | | 9.12 | | 743.5 |
| 60 | T-4 | H | —SO$_2$CH$_2$CH$_3$ | K | | 13.57 | | 750.4 |
| 61 | T-4 | CH$_3$ | —C(O)(CH$_2$)$_2$CH$_3$ | S | | | | 742.4 |
| 62 | T-4 | H | —C(O)CH$_2$CH$_3$ | L | | 8.18 | | 714.5 |
| 63 | T-4 | H | —C(O)CH$_2$OCH$_3$ | L | | 5.82 | | 730.4 |
| 64 | T-4 | H | —C(O)H | L | 9.06 | 5.92 | | 686.4 |
| 65 | T-4 | H | —C(O)CH$_2$NH$_2$ | L | 4.92 | | | 715.4 |
| 66 | T-4 | CH$_3$ | —SO$_2$CH$_2$C(O)OCH$_3$ | K | 12.97 | | | 808.5 |
| 67 | T-4 | CH$_3$ | —C(O)CH$_2$N(CH$_3$)$_2$ | AD | 6.03 | | | 757.5 |
| 68 | T-4 | CH$_3$ | —C(O)CF$_3$ | AD | | | | 768.4 |
| 69 | T-4 | CH$_3$ | 2-furoyl | AD | 12.42 | | | 766.4 |
| 70 | T-4 | CH$_3$ | —CH$_2$C(O)CH$_3$ | AB | 6.43 | | | 728.4 |
| 71 | T-8 | CH$_3$ | —C(=CH$_2$)CH$_3$ | X | | 9.83 | | 789 |
| 72 | T-4 | CH$_3$ | —CH$_2$CH=CH$_2$ | AE | 7.393 | | | 712.5 |
| 73 | T-4 | CH$_3$ | 4-imidazolylmethylcarbonyl | L | 5.00 | | | 780.4 |
| 74 | T-4 | CH$_3$ | —CH$_2$C(O)OCH$_3$ | AB | 9.42 | | | 744.4 |
| 75 | T-4 | CH$_3$ | 2-benzofuranylcarbonyl | AD | 16.32 | | | 816.1 |
| 76 | T-4 | CH$_3$ | —C(O)CH$_2$NHC(O)(phenyl) | AD | 12.66 | | | 833.1 |
| 77 | T-4 | CH$_3$ | 2-methoxybenzoyl | AD | 13.39 | | | 806.1 |
| 78 | T-4 | CH$_3$ | 2-thienylcarbonyl | AD | 13.68 | | | 782.3 |
| 79 | T-4 | CH$_3$ | 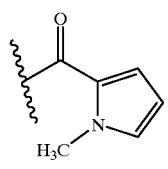 | AD | 13.46 | | | 779.4 |
| 80 | T-4 | CH$_3$ | —C(O)CH$_2$NHC(O)CH$_3$ | AD | 7.87 | | | 771.4 |
| 81 | T-4 | CH$_3$ | benzyl | AB | 10.54 | | | 762.6 |
| 82 | T-4 | CH$_3$ | benzoyl | AD | 13.65 | | | 776.1 |
| 83 | T-4 | CH$_3$ | 2-hydroxyethyl | H | 4.39 | | | 716.4 |
| 84 | T-4 | CH$_3$ | 3,5-dimethoxybenzoyl | AD | 14.42 | | | 836.6 |
| 85 | T-4 | H | 2-furoyl | AD | 11.75 | | | 752.5 |
| 86 | T-4 | H | —C(O)CH$_2$N(CH$_3$)$_2$ | AD | 5.48 | | | 743.5 |
| 87 | T-4 | CH$_3$ | —C(O)CH$_2$(1-imidazolyl) | AD | 7.31 | | | 780.6 |
| 88 | T-4 | CH$_3$ | 3-furoyl | AD | 12.08 | | | 766.5 |
| 89 | T-8 | H | —C(=CH$_2$)CH$_3$ | Y | | | | 774 |
| 90 | T-4 | CH$_3$ | 3-furylmethyl | AC | 9.06 | | | 752.2 |
| 91 | T-4 | | Y¹ and Y² are both 4-methoxybenzyl | AB | | | | 898.8 |
| 92 | T-4 | H | 4-methoxybenzyl | AB | 10.40 | | | 778.6 |
| 93 | T-4 | | Y¹ and Y² are both 4-chlorobenzyl | AB | 23.99 | | | 906.6 |
| 94 | T-4 | H | 4-chlorobenzyl | AB | 12.30 | | | 782.5 |
| 95 | T-4 | | Y¹ and Y² are both 3-methoxybenzyl | AB | 16.25 | | | 898.7 |
| 96 | T-4 | H | 3-methoxybenzyl | AB | 10.76 | | | 778.6 |
| 97 | T-8 | H | 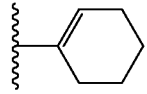 | Z | | | 44.14 | 816 |
| 98 | T-4 | CH$_3$ | 4-methoxybenzyl | AB | 10.72 | | | 792.5 |
| 99 | T-4 | CH$_3$ | 4-chlorobenzyl | AB | 12.78 | | | 796.4 |
| 100 | T-4 | H | benzyl | AB | | | | 748.5 |
| 101 | T-4 | | Y¹ and Y² are both benzyl | AB | 14.81 | | | 838.5 |
| 102 | T-4 | H | 2-pyridylmethyl | AB | 7.46 | | | 749.5 |
| 103 | T-4 | H | 2-quinoxaloyl | AD | 13.07 | | | 814.5 |
| 104 | T-4 | CH$_3$ | 4-biphenylmethyl | AB | 15.18 | | | 838.5 |

TABLE 1-continued

| Ex. | T | Y¹ | Y² | P | HPLC I | HPLC II | HPLC III | Mass Spec. |
|---|---|---|---|---|---|---|---|---|
| 105 | T-4 | H | 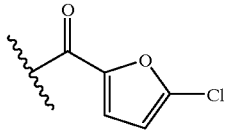 | AD | 14.09 | | | 786.4 |
| 106 | T-4 | H | 3,4-dichloro-2-furoyl | AD | | | | 820.3 |
| 107 | T-4 | H | 3-methyl-2-furoyl | AD | 13.27 | | | 766.4 |
| 108 | T-4 | H | 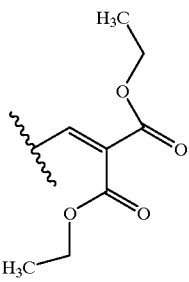 | AO | 14.5 | | | 828.5 |
| 109 | T-4 | H | 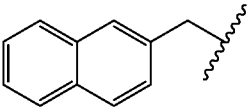 | AB | 13.03 | | | 798.5 |
| 110 | T-4 | H | 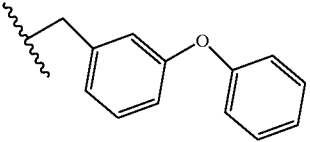 | AB | 14.97 | | | 840.3 |
| 111 | T-4 | H | 2-thienylcarbonyl | AD | 12.87 | | | 768.4 |
| 112 | T-4 | H | 2-pyrrolylcarbonyl | AD | 11.97 | | | 751.5 |
| 113 | T-4 | H | 3-methoxybenzoyl | AD | 13.48 | | | 792.5 |
| 114 | T-4 | H | 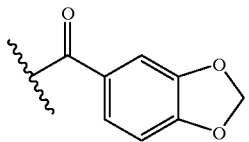 | AD | 13.04 | | | 806.5 |
| 115 | T-4 | H | 4,5-dimethyl-2-furoyl | AD | 14.23 | | | 780.5 |
| 116 | T-4 | H | 4-biphenylcarbonyl | AD | | | | 838.6 |
| 117 | T-4 | H | benzyloxycarbonylmethyl | AB | 14.84 | | | 806.6 |
| 118 | T-4 | H | 3-furoyl | AD | | | | 752.6 |
| 119 | T-4 | H | benzoyl | AD | 12.58 | | | 762.5 |
| 120 | T-4 | H | 4-bromobenzoyl | AD | 15.66 | | | 840.5 |
| 121 | T-4 | CH₃ | 2-hydroxy-3-methoxybenzyl | AC | 10.38 | | | 808.5 |
| 122 | T-4 | H | 4-methoxybenzoyl | AD | 13.29 | | | 792.5 |
| 123 | T-4 | H | 2-chloro-3-pyridylcarbonyl | AD | 11.11 | | | 797.4 |
| 124 | T-4 | H | 2,3-dichloro-5-pyridylcarbonyl | AD | 15.25 | | | 831.4 |
| 125 | T-4 | H | 1-methyl-2-pyrrolylcarbonyl | AD | 12.88 | | | 765.5 |
| 126 | T-4 | H | 2-hydroxy-6-pyridylcarbonyl | AD | 8.44 | | | 779.5 |
| 127 | T-4 | H | 2-pyrazinylcarbonyl | AD | 9.44 | | | 764.5 |
| 128 | T-4 | H | 2-thienylsulfonyl | AD | | | | |
| 129 | T-4 | | Y¹ and Y² are both 2-thienylsulfonyl | AD | 24.03 | | | 949.9 |
| 130 | T-4 | CH₃ | 4-hydroxy-3-methoxy-benzyl | AC | 8.23 | | | 808.5 |
| 131 | T-4 | CH₃ | 4-acetamidobenzyl | AB | 7.68 | | | 819.6 |

TABLE 1-continued

| Ex. | T | Y¹ | Y² | P | HPLC I | HPLC II | HPLC III | Mass Spec. |
|---|---|---|---|---|---|---|---|---|
| 132 | T-4 | H | (6-substituted uracil group) | AB | 7.25 | | | 782.5 |
| 133 | T-4 | H | 2-pyridylcarbonyl | AD | 9.96 | | | 763.4 |
| 134 | T-4 | CH₃ | 3-chloro-4-hydroxy-5-methoxy benzyl | AC | 10.21 | | | 842.5 |
| 135 | T-4 | H | 2-quinolinylcarbonyl | AD | 13.44 | | | 813.4 |
| 136 | T-4 | CH₃ | (furyl enone group) | AD | 14.25 | | | 792.5 |
| 137 | T-4 | CH₃ | 2-phenylethylcarbonyl | AD | 14.99 | | | 804.5 |
| 138 | T-4 | CH₃ | (phenyl enone group) | AD | 24.051 | | | 802.5 |
| 139 | T-4 | CH₃ | 2-quinolinylmethyl | AB | 11.90 | | | 813.7 |
| 140 | T-4 | CH₃ | 4-quinolinylmethyl | AC | 12.82 | | | 813.7 |
| 141 | T-4 | CH₃ | 4-cyanobenzyl | AC | | | | 787.8 |
| 142 | T-4 | H | (5-formylfuran-2-ylcarbonyl group) | AD | 11.37 | | | 780.7 |
| 143 | T-4 | CH₃ | 4-nitrobenzyl | AB | 13.09 | | | 807.6 |
| 144 | T-4 | CH₃ | benzylcarbonyl | AD | 14.03 | | | 790.5 |
| 145 | T-4 | H | 2-quinolinylmethyl | AB | 11.45 | | | 799.2 |
| 146 | T-4 | H | 4-quinolinylmethyl | AC | 11.62 | | | 799.2 |
| 147 | T-4 | H | (2-thienylmethyl ketone group) | AD | 13.20 | | | 782.5 |
| 148 | T-4 | | Y¹ and Y² are both 2-quinolinylmethyl | AB | 19.03 | | | 940.1 |
| 149 | T-4 | CH₃ | benzyloxycarbonylmethyl | AB | 15.73 | | | 820.8 |
| 150 | T-4 | CH₃ | 2-methoxybenzyl | AB | 11.16 | | | 792.8 |
| 151 | T-4 | CH₃ | 3-methoxybenzyl | AB | 11.11 | | | 792.5 |
| 152 | T-4 | CH₃ | 2-pyridylmethyl | AB | 7.88 | | | 763.7 |
| 153 | T-4 | CH₃ | 3-pyridylmethyl | AB | 7.27 | | | 763.7 |
| 154 | T-4 | H | (phenyl enone group) | AD | 15.28 | | | 788.5 |

TABLE 1-continued

| Ex. | T | Y¹ | Y² | P | HPLC I | HPLC II | HPLC III | Mass Spec. |
|---|---|---|---|---|---|---|---|---|
| 155 | T-4 | H | (E)-3-(2-furyl)acryloyl | AD | 13.75 | | | 778.5 |
| 156 | T-4 | H | 2-phenylethylcarbonyl | AD | 14.41 | | | 790.5 |
| 157 | T-4 | H | benzylcarbonyl | AD | 13.64 | | | 776.6 |
| 158 | T-4 | CH₃ | 2-quinoxaloyl | AD | 13.68 | | | 828.5 |
| 159 | T-4 | CH₃ | 2-quinolinylcarbonyl | AD | 14.07 | | | 827.5 |
| 160 | T-4 | CH₃ | 4-quinolinylcarbonyl | AD | 12.33 | | | 827.5 |
| 161 | T-4 | H | 4-quinolinylcarbonyl | AD | 11.81 | | | 813.7 |
| 162 | T-4 | CH₃ | 2-pyridylcarbonyl | AD | 10.43 | | | 777.6 |
| 163 | T-4 | H | 3-pyridylcarbonyl | AD | 9.54 | | | 763.4 |
| 164 | T-4 | CH₃ | 3-pyridylcarbonyl | AD | 9.93 | | | 777.5 |
| 165 | T-4 | H | 4-imidazolylcarbonyl | AD | | | | 752.6 |
| 166 | T-4 | CH₃ | 3,4-dichlorobenzyl | AB | 15.76 | | | 830.4 |
| 167 | T-4 | H | 3,4-dichlorobenzyl | AB | 14.62 | | | 816.5 |
| 168 | T-4 | CH₃ | 3,5-difluorobenzyl | AB | 13.37 | | | 798.5 |
| 169 | T-4 | CH₃ | 4-fluorobenzyl | AB | 11.28 | | | 780.6 |
| 170 | T-4 | CH₃ | 4-pyridylmethyl | AB | 8.09 | | | 763.6 |
| 171 | T-4 | H | 4-pyridylcarbonyl | AD | 9.51 | | | 763.6 |
| 172 | T-4 | CH₃ | 4-pyridylcarbonyl | AD | 9.90 | | | 777.6 |
| 173 | T-4 | CH₃ | 4-trifluoromethylbenzyl | AB | 14.78 | | | 830.5 |
| 174 | T-4 | H | 4-trifluoromethylbenzyl | AB | 13.83 | | | 816.6 |
| 175 | T-4 | H | —C(O)C(O)CH₃ | AD | 11.19 | | | 728.4 |
| 176 | T-4 | CH₃ | 3-hydroxy-4-methoxybenzyl | AC | | | | 808.5 |
| 177 | T-4 | CH₃ | 2-oxo-3-(phenylamino)propyl | AD | | | | 805.6 |
| 178 | T-4 | H | 5-nitro-2-furoyl | AD | 13.82 | | | 797.7 |
| 179 | T-4 | H | 4-methoxybenzylcarbonyl | AD | 13.44 | | | 806.6 |
| 180 | T-4 | H | 2-hydroxybenzylcarbonyl | AD | 12.67 | | | 792.4 |
| 181 | T-4 | H | 3,5-difluorobenzyl | AB | 12.44 | | | 784.5 |
| 182 | T-4 | H | 2-methoxybenzylcarbonyl | AD | 13.92 | | | 806.6 |
| 183 | T-4 | H | 4-hydroxybenzylcarbonyl | AD | 10.73 | | | 793.5 |
| 184 | T-4 | H | 3-hydroxybenzylcarbonyl | AD | 11.24 | | | 792.5 |
| 185 | T-4 | CH₃ | 3-(phthalimido)propyl | AC | | | | 854 |
| 186 | T-4 | H | 3-methoxyphenoxymethyl-carbonyl | AD | | | | 822.8 |
| 187 | T-4 | CH₃ | benzoylmethyl | AB | 11.70 | | | 790.6 |
| 188 | T-4 | CH₃ | 2-(dimethylamino)-3-phenylpropanoyl | AD | 9.77 | | | 847.7 |
| 189 | T-4 | CH₃ | 1-methylprolyl | AD | 6.84 | | | 783.6 |

TABLE 1-continued

| Ex. | T | Y¹ | Y² | P | HPLC I | HPLC II | HPLC III | Mass Spec. |
|---|---|---|---|---|---|---|---|---|
| 190 | T-4 | H | 2-indenylcarbonyl | AD | 15.43 | | | 801.5 |
| 191 | T-4 | H | 3-indenylcarbonyl | AD | 13.21 | | | 801.4 |
| 192 | T-4 | CH₃ | 2-(bis(2-methoxybenzyl)amino)ethyl | AC | | | | 955 |
| 193 | T-4 | H | (2-furyl-dicarbonyl structure) | AD | | | | 780.5 |
| 194 | T-4 | CH₃ | diphenylphosphinyl | AG | 15.80 | | | 782.5 |
| 195 | T-4 | CH₃ | (benzylaminomethyl ketone structure) | AD | 9.90 | | | 819.6 |
| 196 | T-4 | CH₃ | (N-methyl-N-benzylaminomethyl ketone structure) | AD | | | | 833.6 |
| 197 | T-4 | H | (phenyl-1,2-diketone structure) | AD | 15.53 | | | 804.5 |
| 198 | T-4 | CH₃ | 2-phenylethyl | AC | 12.24 | | | 776.5 |
| 199 | T-4 | CH₃ | 3-(4-hydroxyphenyl)-2-propenyl | AC | 13.11 | | | 818.6 |
| 200 | T-4 | H | 4-methoxyphenoxymethyl-carbonyl | AD | 14.05 | | | 822.9 |
| 201 | T-4 | H | 2-methoxyphenoxymethyl-carbonyl | AD | 13.89 | | | 822.9 |
| 202 | T-4 | H | phenoxymethylcarbonyl | AD | 14.48 | | | 792.5 |
| 203 | T-4 | CH₃ | 2-(bis(2-phenylethyl)amino)ethyl | AC | | | | 923 |
| 204 | T-4 | H | 4-methylbenzyl | AB | 11.27 | | | 762.5 |
| 205 | T-4 | H | 2-phenoxyethylcarbonyl | AD | 14.87 | | | 806.9 |
| 206 | T-4 | H | 2-chlorophenoxymethyl-carbonyl | AD | | | | 826.4 |
| 207 | T-8 | CH₃ | (cyclohexenyl structure) | Z | 18.55 | | | 829 |
| 208 | T-8 | H | (cyclopentenyl structure) | AA | | | 31.73 | 802 |
| 209 | T-7 | H | (cyclopentenyl structure) | A | | 21.62 | | 672 |

TABLE 1-continued

| Ex. | T | Y¹ | Y² | P | HPLC I | HPLC II | HPLC III | Mass Spec. |
|---|---|---|---|---|---|---|---|---|
| 210 | T-7 | $CH_3$ | cyclohexenyl | A | 13.27 | | | 672 |
| 211 | T-7 | H | cyclohexenyl | A | 13.35 | | | 657 |
| 212 | T-8 | H | 3,6-dihydro-2H-pyran-4-yl | AA | | | 9.63 | 818 |
| 213 | T-7 | H | 3,6-dihydro-2H-pyran-4-yl | B | | 6.05 | | 659.5 |
| 214 | T-7 | H | 1,2,3,6-tetrahydropyridin-4-yl | G | | 3.29 | | 658.4 |
| 215 | T-4 | $CH_3$ | (see structure) | AO | 14.85 | | | 903.2 |
| 216 | T-4 | $CH_3$ | (see structure) | AB | 15.59 | | | 808.3 |

TABLE 1-continued

| Ex. | T | Y$^1$ | Y$^2$ | P | HPLC I | HPLC II | HPLC III | Mass Spec. |
|---|---|---|---|---|---|---|---|---|
| 217 | T-4 | CH$_3$ | | AB | 14.52 | | | 938.5 |
| 218 | T-4 | CH$_3$ | | AB | 15.36 | | | 868.6 |
| 219 | T-4 | CH$_3$ | | AB | | | | 872.2 |
| 220 | T-4 | CH$_3$ | | L | 18.12 | | | 866.5 |

TABLE 1-continued
| Ex. | T | Y¹ | Y² | P | HPLC I | HPLC II | HPLC III | Mass Spec. |
|---|---|---|---|---|---|---|---|---|
| 221 | T-4 | CH₃ | 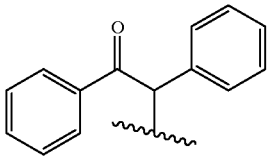 | AB | 16.95 | | | 866.6 |
| 222 | T-4 | CH₃ | 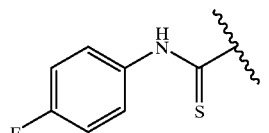 | AO | 16.59 | | | 825.7 |
| 223 | T-4 | CH₃ | 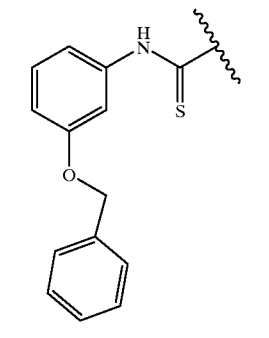 | AO | 20.59 | | | 913.6 |
| 224 | T-4 | CH₃ | 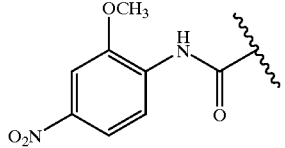 | AO | 17.03 | | | 866.3 |
| 225 | T-4 | H | 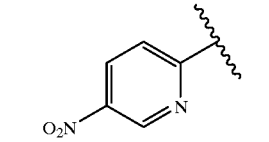 | AF | 16.14 | | | 780.5 |
| 226 | T-4 | H | 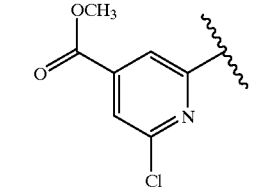 | AF | 19.25 | | | 827.5 |
| 227 | T-4 | H | 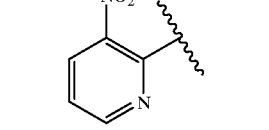 | AF | 15.96 | | | 780.5 |

In Table 2 below, all compounds are based on the T-4 macrolide template illustrated above.

TABLE 2

| Ex. | Y$^1$ | Y$^2$ | P | Mass Spec. |
|---|---|---|---|---|
| 228 | | Y$^1$ is benzyl; Y$^2$ is 2-pyrazinecarbonyl | AK | 854.5 |
| 229 | | Y$^1$ is 4-methoxybenzyl, Y$^2$ is 2-pyrazinecarbonyl | AL | 884.5 |
| 230 | CH$_3$ | (4-oxo-4H-chromen-2-yl)carbonyl | AD | 844.6 |
| 231 | H | (4-oxo-4H-chromen-2-yl)carbonyl | AD | 830.8 |
| 232 | H | 7,8-difluoro-3-quinolinecarbonyl | AD | 849.6 |
| 233 | H | 3-quinolinecarbonyl | AD | 813.8 |
| 234 | H | 3-hydroxy-4-methoxybenzoyl | AD | 808.6 |
| 235 | CH$_3$ | 2-pyrazinecarbonyl | AD | 778.6 |
| 236 | H | 3-(4-chlorophenoxy)propionyl | AD | 840.7 |
| 237 | H | 4-(4-chlorophenoxy)butanoyl-type | AD | 808.7 |
| 238 | H | 4-acetamidobenzoyl | AD | 819.7 |
| 239 | H | (E)-4-(2-hydroxyphenyl)-4-oxo-2-butenamido-acetyl | AD | 887.6 |

TABLE 2-continued
| Ex. | Y¹ | Y² | | P | Mass Spec. |
|---|---|---|---|---|---|
| 240 | H | 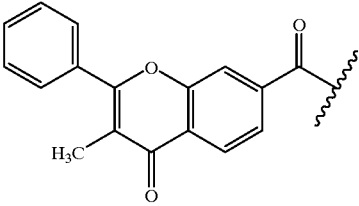 | | AD | 920.6 |
| 241 | H | 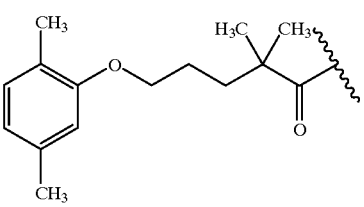 | | AD | 890.1 |
| 242 | H | 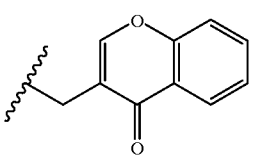 | | AC | 830.1 |
| 243 | H | 1-isoquinolinecarbonyl | | AD | 813.1 |
| 244 | H | 3-isoquinolinecarbonyl | | AD | 813.1 |
| 245 | H | 4-methoxy-2-quinolinecarbonyl | | AD | 843.1 |
| 246 | H | 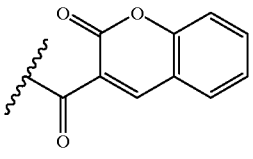 | | AD | 830.2 |
| 247 | H | 4-cinnolinecarbonyl | | AD | 814.2 |
| 248 | H | 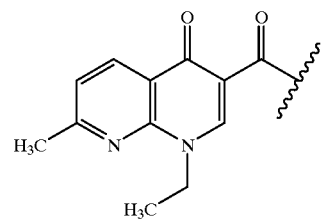 | | AD | 872.2 |
| 249 | H | 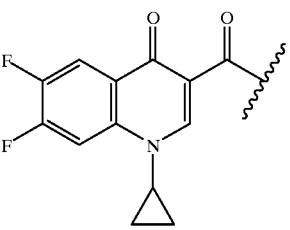 | | AD | 905.1 |
| 250 | H | 3,4-dihydroxybenzyl | | AC | 794.2 |
| 251 | H | 2-hydroxy-3-quinoxalinecarbonyl | | AD | 830.1 |
| 252 | H | 2-(1-pyrrole)-5-pyridylcarbonyl | | AD | 828.2 |

TABLE 2-continued
| Ex. | Y¹ | Y² | P | Mass Spec. |
|---|---|---|---|---|
| 253 | H | 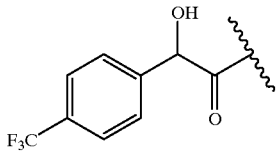 | AD | 860.1 |
| 254 | H | 3-benzyloxy-4-methoxybenzoyl | AD | 898.6 |
| 255 | H | 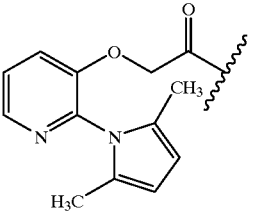 | AD | 886.6 |
| 256 | CH₃ | 3-benzyloxy-4-methoxybenzyl | AB | 898.6 |
| 257 | H | 3,4-difluorobenzoyl | AD | 798.6 |
| 258 | H | 2,4-difluorobenzoyl | AD | 798.7 |
| 259 | H | 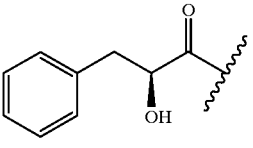 | AD | 806.2 |
| 260 | H | tert-butylcarbonyl | AD | 742.2 |
| 261 | H | 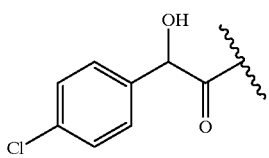 | AD | 826.2 |
| 262 | H | 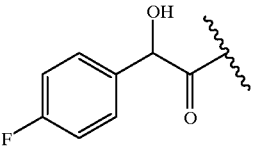 | AD | 810.1 |
| 263 | H | 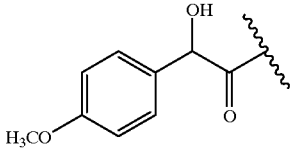 | AD | 822.6 |
| 264 | H | 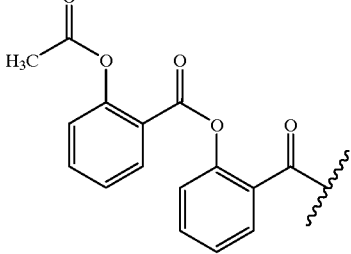 | AD | 940.1 |

TABLE 2-continued

| Ex. | Y$^1$ | Y$^2$ | P | Mass Spec. |
|---|---|---|---|---|
| 265 | H | 4-methoxy-3-(dimethyl-(tert-butyl)silyloxy)benzyl | AB | 908.6 |
| 266 | H | 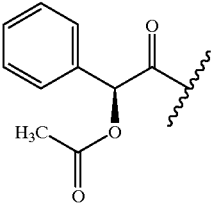 | AD | 834.7 |
| 267 | H | 5-benzimidazolecarbonyl | AD | 802.6 |
| 268 | H | 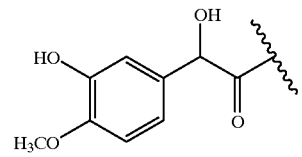 | AD | 838.7 |
| 269 | H | 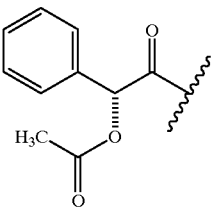 | AD | 834.6 |
| 270 | H | 2-benzofurancarbonyl | AD | 802.6 |
| 271 | H | 4-acetamidobenzyl | AB | 805.6 |
| 272 | | Both Y$^1$ and Y$^2$ are 4-acetamidobenzyl | AB | |
| 273 | CH$_3$ | 2-benzofurancarbonyl | AB | 802.6 |
| 274 | CH$_3$ | 3-isobutoxy-4-methoxybenzyl | AB | 864.6 |
| 275 | CH$_3$ | 4-methoxy-3-(4-trifluoromethylbenzyloxy)benzyl | AB | 966.6 |
| 276 | H | 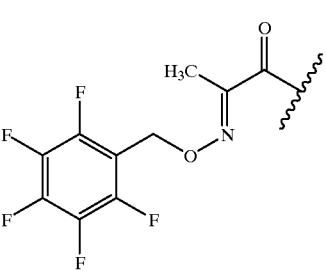 | AN | 923.5 |
| 277 | H | 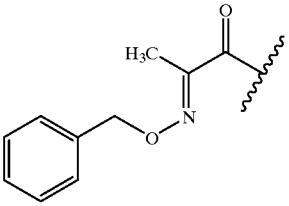 | AM | 833.6 |
| 278 | CH$_3$ | 2-benzimidazolemethyl | AB | 802.5 |
| 279 | H | 4-benzyloxycarbonyl-2-fluorophenyl | AH | 886.6 |
| 280 | H | 3-hydroxy-4-methoxybenzyl | AC | 794.6 |
| 281 | H | 3,6-dichloro-4-pyridazinecarbonyl | AD | 832.6 |

TABLE 2-continued
| Ex. | Y¹ | Y² | | P | Mass Spec. |
|---|---|---|---|---|---|
| 282 | H | 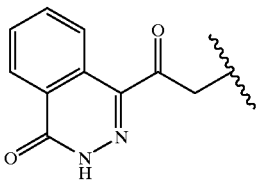 | | AD | 844.6 |
| 283 | CH₃ | 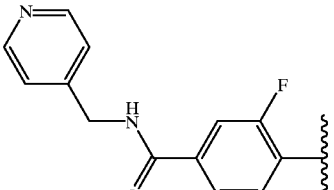 | | AI | 900.5 |
| 284 | H | 4-pyridylcarbonyl | | AB | 749.1 |
| 285 | H | 3-pyridylcarbonyl | | AB | 749.1 |
| 286 | CH₃ | 3-quinolinecarbonyl | | AD | 827.1 |
| 287 | H | 3-bis(methylsulfonyl)aminobenzyl | | AB | 919 |
| 288 | H | 3-ethoxy-4-hydroxybenzyl | | AC | 808.1 |
| 289 | H | 3-methoxy-4-hydroxybenzyl | | AC | 794.1 |
| 290 | CH₃ | 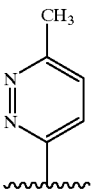 | | AQ | 764.02 |
| 291 | CH₃ | 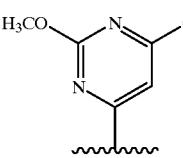 | | AQ | 810.05 |
| 292 | CH₃ | 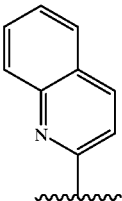 | | AQ | 799.06 |
| 293 | CH₃ | 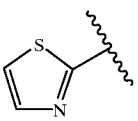 | | AQ | NT |

TABLE 2-continued
| Ex. | Y¹ | Y² | | P | Mass Spec. |
|---|---|---|---|---|---|
| 294 | CH₃ | 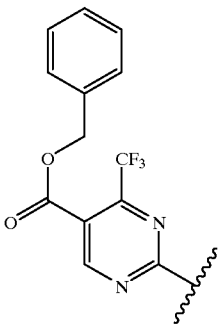 | | AQ | 952.13 |
| 295 | CH₃ | 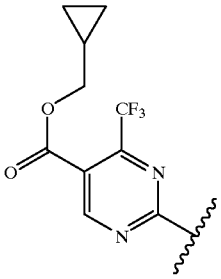 | | AQ | 916.1 |
| 296 | CH₃ | 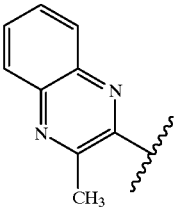 | | AQ | 814.09 |
| 297 | CH₃ | 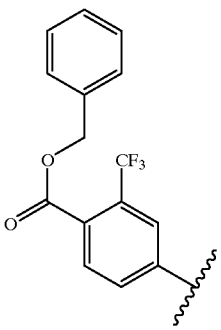 | | AP | 950.16 |

TABLE 2-continued
| Ex. | Y¹ | Y² | P | Mass Spec. |
|---|---|---|---|---|
| 298 | $CH_3$ | 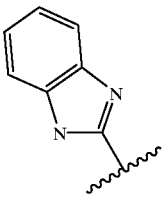 | AQ | 788.05 |
| 299 | $CH_3$ | 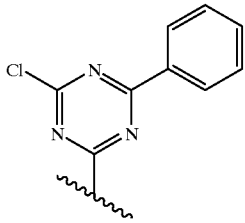 | AQ | 861.52 |
| 300 | $CH_3$ | 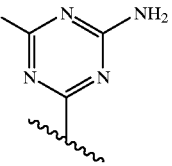 | AQ | 781.04 |
| 301 | H | 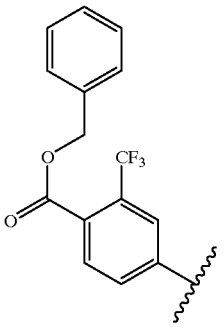 | AP | 936.16 |
| 302 | $CH_3$ | 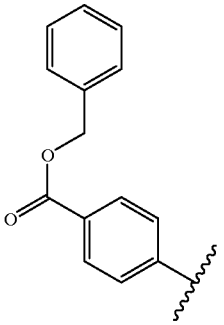 | AP | 883.5 |

We claim:
1. A compound of the formula 1 or 2

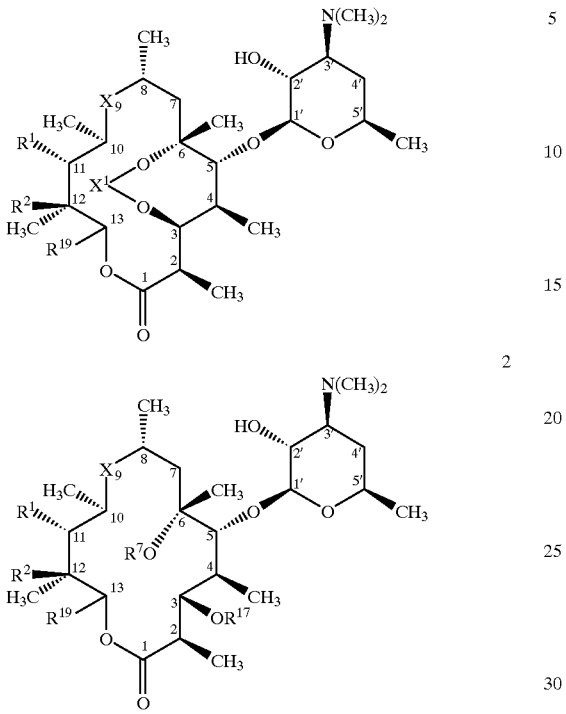

or a pharmaceutically acceptable salt or solvate thereof, wherein:

X is —CH(—NR$^9$R$^{10}$)—, —CH(OR$^3$)—, —C(O)—, —CH$_2$NR$^6$—, —NR$^6$CH$_2$—, or —C(=NR$^5$)—, wherein the first dash of each of the foregoing X groups is attached to the C-10 carbon of the compounds of formulas 1 and 2 and the last dash of each group is attached to the C-8 carbon of the compounds of formulas 1 and 2;

R$^1$ and R$^2$ are each OH;
or R$^2$ is O and R$^1$ is X$^2$, and they are taken together as follows:

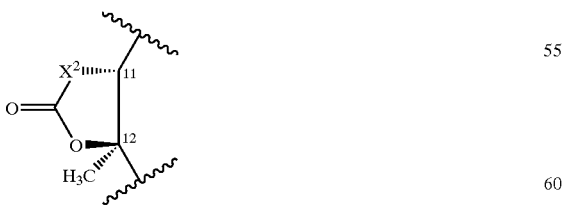

wherein X$^2$ is O, —N(R$^7$)—, or —N(NR$^7$R$^8$)—;
each R$^3$ and R$^{3'}$ is independently selected from the group consisting of H, C$_1$-C$_6$ alkyl, —(CH$_2$)$_m$ (C$_6$-C$_{10}$ aryl), and —(CH$_2$)$_m$(4–10 membered heterocyclic), wherein m is an integer ranging from 0 to 4 and the foregoing R$^3$ groups are optionally substituted by 1 to 3 R$^{13}$ groups;

R$^4$ is selected from the group of substituents provided in the definition of R$^3$ or R$^4$ is —OR$^7$;
or R$^3$ and R$^4$ are taken together with the carbon to which each is attached to form a ring defined by X$^3$, X$^4$ and X$^5$ as follows

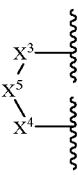

wherein X$^3$ and X$^4$ are each independently —(CHR$^{16}$)$_n$— wherein n is an integer ranging from 1to 4;
X$^5$ is S, O, —CHR$^6$—) or —N(R$^6$)—;
R$^5$ is hydroxy, C$_1$-C$_6$, alkyl, C$_1$-$_6$ alkoxy, —(CH$_2$)$_m$(C$_6$-C$_{10}$ aryl), —(CH$_2$)$_m$(4–10 membered heterocyclic), or (C$_2$)$_m$O(CH$_2$)$_z$OR$^7$, wherein m is an integer ranging from 0 to 4 and z is an integer ranging from 2 to 6, and the foregoing R$^5$ groups, except hydroxy, are optionally substituted by 1 to 3 R$^{13}$ groups;
R$^6$ is H, hydroxy, formyl, C$_1$-C$_{10}$ alkoxy, C$_1$-C$_{10}$ alkyl, C$_2$-C$_{10}$ alkenyl, —SO$_2$(C$_1$-C$_{10}$ alkyl), —(C$_2$)$_m$C(O)CH$_2$OC(O)(C$_1$-C$_{10}$ akyl), —(CH$_2$)$_m$C(O)(CH$_2$)$_t$NR$^{11}$R$^{12}$, —(CH$_2$)$_t$C(O) (C$_1$-C$_{10}$ alkyl), —(CH$_2$)$_m$C(O)(CH$_2$)$_t$C(O) (C$_1$-C$_{10}$ alkyl), —(CH$_2$)$_m$C(O)(CH$_2$)$_t$O (C$_1$-C$_{10}$ alkyl), —(CH$_2$)$_m$C(O)(CH$_2$)$_t$O (C$_2$-C$_{10}$ alkenyl), —(CH$_2$)$_t$(C$_6$-C$_{10}$ aryl), —(CH$_2$)$_t$(4–10 membered heterocyclic), —C(O)(CH$_2$)$_m$C(O)(CH$_2$)$_q$(C$_6$-C$_{10}$ aryl), —C(O)(CH$_2$)$_m$C(O)(CH$_2$)$_q$(4–10 membered heterocylic), —(CH$_2$)$_m$C(O)(CH$_2$)$_q$(C$_6$-C$_{10}$ aryl), —(CH$_2$)$_m$C(O)(CH$_2$)$_q$(4–10 membered heterocyclic), —(CH$_2$)$_q$C(O)(CH$_2$)$_m$O(CH$_2$)$_t$ (C$_6$-C$_{10}$ aryl), —(CH$_2$)$_q$C(O)(CH$_2$)$_m$O(CH$_2$)$_t$ (4–10 membered heterocyclic), —(CH$_2$)$_t$O (CH$_2$)$_m$(C$_6$-C$_{10}$ aryl), —(CH$_2$)$_t$O(CH$_2$)$_m$(4–10 membered heterocyclic), —(CH$_2$)$_m$P(O) R$^3$R$^{16}$, —SO$_2$(CH$_2$)$_t$(C$_6$-C$_{10}$ aryl), or —SO$_2$ (CH$_2$)$_t$(4–10 membered heterocyclic), —(CH$_2$)$_m$C(S)(CH$_2$)$_t$NR$^{11}$R$^{12}$, wherein m is an integer ranging from 0 to 4, q and t are each independently an integer ranging from 0 to 5, the —(CH$_2$)$_q$— moiety of the above R$^6$ groups optionally includes a carbon-carbon double bond where q is 2 or greater, the heterocyclic moieties of the above R$^6$ groups optionally include an oxo (=O) group on the ring system, and the foregoing R$^6$ groups, except H, formyl and hydroxy, are optionally substituted by 1 to 3 R$^{13}$ groups;
each R$^7$ and R$^8$ is independently H or C$_1$-C$_6$ alkyl;
R$^9$ and R$^{10}$ are each independently selected from the group consisting of H, C$_1$-C$_6$ alkyl, —C(=NR$^5$)NR$^7$R$^8$, and —C(O)R$^7$, or R$^9$ and R$^{10}$ are taken together to form =CH(CH$_2$)$_m$ (C$_6$-C$_{10}$ aryl, =CH(CH$_2$)$_m$(4–10 membered heterocyclic), =CR$^7$R$^8$, or =C(R$^7$)C(O)OR$^8$, wherein m is an integer ranging from 0 to 4, and the alkyl, aryl and heterocyclic moieties of the foregoing $R^9$ and $R^{10}$ groups are optionally substituted by 1 to 3 $R^{13}$ groups;

$R^{11}$ and $R^{12}$ are each independently selected from the group consisting of H, $C_1$–$C_{10}$ alkyl, $C_2$–$C_{10}$ alkenyl, —C(O)($C_1$–$C_{10}$ alkyl), —(CH$_2$)$_m$($C_6$–$C_{10}$ aryl), —C(O)(CH$_2$)$_m$ ($C_6$–$C_{10}$ aryl), —(CH$_2$)$_m$(4–10 membered heterocyclic), and —C(O)(CH$_2$)$_m$(4–10 membered heterocyclic), wherein m is an integer ranging from 0 to 4, and the foregoing $R^{11}$ and $R^{12}$ groups, except H, are optionally substituted by 1 to 3 $R^{13}$ groups;

each $R^{13}$ is independently selected from the group consisting of halo, cyano, nitro, trifluoromethyl, azido, —C(O)$R^{16}$, —C(O)O$R^{16}$, —OC(O)$R^{16}$, —OC(O)O$R^{16}$, —NR$^{14}$C(O)$R^{15}$, —C(O)NR$^{14}$R$^{15}$, —NR$^{14}$R$^{15}$, hydroxy, $C_1$–$C_6$ alkyl, —N(SO$_2$R$^{16}$)$_2$, —NR$^{14}$SO$_2$R$^{16}$, —S(O)$_j$($C_1$–$C_6$ alkyl) wherein j is an integer ranging from 0 to 2, $C_1$–$C_6$ alkoxy, —(CH$_2$)$_m$($C_6$–$C_{10}$ aryl), and —(CH$_2$)$_m$(4–10 membered heterocyclic), wherein m is an integer ranging from 0 to 4, and the alkyl, alkoxy, aryl and heterocyclic moieties of the above $R^{13}$ subsituents are optionally substituted by 1 to 3 substituents independently selected from the group consisting of halo, cyano, nitro, trifluoromethyl, azido, —C(O)$R^{16}$, —C(O)O$R^{16}$, —CO(O)$R^{16}$, —OC(O)O$R^{16}$, —NR$^{14}$C(O)$R^{15}$, —C(O)NR$^{14}$R$^{15}$,—NR$^{14}$R$^{15}$, hydroxy $C_1$–$C_6$ alkyl, and $C_1$–$C_6$ alkoxy;

each $R^{14}$ and $R^{15}$ is independently H, —OR$^7$, $C_1$–$C_6$ alkyl, —(CH$_2$)$_m$($C_6$–$C_{10}$ aryl), or —(CH$_2$)$_m$(4–10 membered heterocyclic), wherein m is an integer ranging from 0 to 4, with the proviso that where $R^{14}$ and $R^{15}$ are both attached to the same nitrogen, then $R^{14}$ and $R^{15}$ are not both —OR$^7$;

each $R^{16}$ is independently selected from the group consisting of H, $C_1$–$C_{10}$ alkyl, —(CH$_2$)$_m$($C_6$–$C_{10}$ aryl), and —(CH$_2$)$_m$(4–10 membered heterocyclic), wherein m is an integer ranging from 0 to 4; and, $R^{17}$ is selected from the group of substituents provided in the definition of $R^{18}$ or $R^{17}$ is a group of the formula

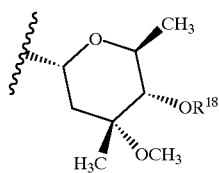

$R^{18}$ is —CR$^3$=CR$^{3'}$R$^4$ or a group of the formula

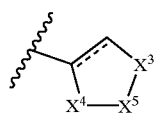

wherein the dashed line represents an optional double bond; and $R^{19}$ is ethyl, an alpha-branched $C_3$–$C_6$ alkyl, $C_2$–$C_6$ alkenyl, $C_2$–$C_6$ alkynyl, ($C_1$–$C_6$ alkoxy) $C_1$–$C_6$ alkyl, ($C_1$–$C_6$ alkylthio)$C_1$–$C_6$ alkyl, ($C_5$–$C_8$ cycloalkyl)($C_2$–$C_5$ alpha branched a alkyl)-, $C_3$–$C_8$ cycloalkyl, $C_5$–$C_8$ cycloalkenyl, 3–6 membered O or S containing heterocyclic group, or phenyl, wherein each of the foregoing $R^{19}$ groups may be substituted by 1 to 3 substituents independently selected from hydroxy, halo and $C_1$–$C_4$ alkyl.

2. A compound according to claim 1 wherein said compound is a compound of formula 1.

3. A compound according to claim 2 wherein $R^{19}$ is ethyl, X is —NR$^6$CH$_2$— or —CH$_2$NR$^6$—, where $R^6$ is H or methyl.

4. A compound according to claim 3 wherein $R^1$ and $R^2$ are both hydroxy, and $X^1$ is the following cyclic group:

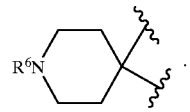

5. A compound according to claim 4 wherein $R^6$ is H, hydroxy, hydroxy substituted $C_1$–$C_{10}$ alkyl, formyl, $C_1$–$C_{10}$ alkoxy, —SO$_2$($C_1$–$C_4$ alkyl), —(CH$_2$)$_m$C(O)($C_1$–$C_{10}$ alkyl), —(CH$_2$)$_m$C(O)CH$_2$OC(O)($C_1$–$C_{10}$ alkyl), —(CH$_2$)$_m$C(O)CH$_2$O($C_1$–$C_{10}$ alkyl), —(CH$_2$)$_m$C(O)(CH$_2$)$_q$($C_6$–$C_{10}$ aryl), —(CH$_2$)$_m$C(O)(CH$_2$)$_q$(4–10 membered heterocyclic), —(CH$_2$)$_t$(4–10 membered heterocyclic), or —(CH$_2$)$_t$($C_6$–$C_{10}$ aryl), wherein m, q and t are each independently 0 or 1.

6. A compound according to claim 4 wherein $R^6$ is selected from the group consisting of: —C(O)CH$_2$CH$_3$, —C(O)CH$_2$OCH$_3$, —C(O)H, —C(O)CH$_2$OH, —C(O)CH$_2$OC(O)CH$_3$, —C(O)CH$_3$, -4-chlorobenzyl, 2-pyridylmethyl, 4-acetamidobenzyl, 4-hydroxy-3-methoxybenzyl, 3-hydroxy-4-methoxybenzyl, 2-hydroxyethyl, —C(O)CH$_2$N(CH$_3$)$_2$, 4-quinolinylmethyl, 2-quinolinylmethyl, —C(O)CH$_2$OC(O)CH$_3$, —SO$_2$CH$_2$CH$_3$, —SO$_2$CH(CH$_3$)$_2$, 2-furoyl, benzoyl, 1-methyl-2-pyrrolylcarbonyl, 2-pyrazinylcarbonyl, 2-pyridylcarbonyl, 2-quinolinylcarbonyl, 3-pyridylcarbonyl, 3-cinnolinecarbonyl, 3-quinolinylcarbonyl, 4-benzyloxycarbonyl-2-fluorophenyl, and

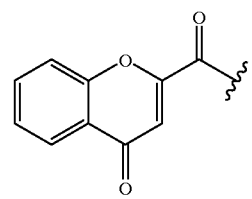

7. A pharmaceutical composition for the treatment of a bacterial, parasitic or protozoal infection, or a disorder related to a bacterial, parasitic or protozoal infection, in a mammal, fish, or bird which comprises a therapeutically effective amount of a compound of claim 1 and a pharmaceutically acceptable carrier.

8. The pharmaceutical composition of claim 7 wherein said infection or disorder is pneumonia, otitis media, sinusitus, bronchitis, tonsillitis, or mastoiditis related to infection by *Streptococcus pneumoniae, Haemophilus* influenzae, Moraxella catarrhalis, Staphylococcus aureus, or Peptostreptococcus spp.; pharynigitis, rheumatic fever, or glomerulonephritis related to infection by *Streptococcus pyogenes*, Groups C and G streptococci, *Clostridium diptheriae*, or *Actinobacillus haemolyticum*; a respiratory tract infections related to infection by *Mycoplasma pneumoniae, Legionella pneumophila; Streptococcus pneumoniae, Haemophilus influenzae*, or *Chlamydia pneumoniae*; uncomplicated skin or soft tissue infection, abscess or osteomyelitis, or puerperal fever related to infection by *Staphylococcus aureus*, coagulase-positive staphylococci (i.e., *S. epidermidis, S. hemolyticus,*), *Streptococcus pyogenes, Streptococcus agalactiae*, Streptococcal groups C-F (minute-colony streptococci), viridans streptococci, *Corynebacterium minutissimum*, Clostridium spp., or *Bartonella henselae*; uncomplicated acute urinary tract infection related to infection by *Staphylococcus saprophyticus* or Enterococcus spp.; urethritis, or cervicitis; a sexually transmitted disease related to infection by *Chlamydia trachomatis, Haemophilus ducreyi, Treponema pallidum, Ureaplasma urealyticum*, or *Neiserria gonorrheae*; toxin disease related to infection by *S. aureus* (food poisoning or toxic shock syndrome), or Groups A, B, and C streptococci; ulcer related to infection by *Helicobacter pylori*; systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by Bordetella pertussis; gas gangrene related to infection by *Clostridium perfringens* or Bacteroides spp.; atherosclerosis or cardiovascular disease related to infection by *Helicobacter pylon* or *Chlamydia pneumoniae*; bovine respiratory disease related to infection by *P. haemolytica, P. multocida, Mycoplasma bovis*, or Bordetella spp.; cow enteric disease related to infection by *E. coli* or protozoa; dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodysinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa; urinary tract infection in a dog or cat related to infection by *E. coli*; skin or soft tissue infection in a dog or cat related to infection by *Staph. epidermidis, Staph. intermedius*, coagulase neg. Staph. or *P. multocida*; or dental or mouth infection in a dog or cat related to infection by Alcaligenes spp., Bacteroides spp., Clostridium spp., Enterobacter spp., Eubacterium, Peptostreptococcus, Porphyromonas, or Prevotella.

9. A method of treating a bacterial, parasitic or protozoal infection, or a disorder related to a bacterial, parasitic or protozoal infection, in a mammal, fish, or bird which comprises administering to said mammal, fish or bird a therapeutically effective amount of a compound of claim 1.

10. The method of claim 9 wherein said infection or disorder is pneumonia, otitis media, sinusitus, bronchitis, tonsillitis, or mastoiditis related to infection by *Streptococcus pneumoniae, Haemophilus influenzae, Moraxella catarrhalis, Staphylococcus aureus*, or Peptostreptococcus spp.; pharynigitis, rheumatic fever, or glomerulonephritis related to infection by *Streptococcus pyogenes*, Groups C and G streptococci, *Clostridium diptheriae*, or *Actinobacillus haemolyticum*; a respiratory tract infections related to infection by *Mycoplasma pneumoniae, Legionella pneumophila, Streptococcus pneumoniae, Haemophilus influenzae*, or *Chlamydia pneumoniae*; uncomplicated skin or soft tissue infection, abscess or osteomyelitis, or puerperal fever related to infection by *Staphylococcus aureus*, coagulase-positive staphylococci (i.e., *S. epidermidis, S. hemolyticus, Streptococcus pyogenes, Streptococcus agalactiae*, Streptococcal groups C-F (minute-colony streptococci), viridans streptococci, *Corynebacterium minutissimum*, Clostridium spp., or *Bartonella henselae*; uncomplicated acute urinary tract infection related to infection by *Staphylococcus saprophyticus* or Enterococcus spp.; urethritis, or cervicitis; a sexually transmitted disease related to infection by *Chlamydia trachomatis, Haemophilus ducreyi, Treponema pallidum, Ureaplasma urealyticum*, or *Neiserria gonorrheae*; toxin disease related to infection by *S. aureus* (food poisoning or toxic shock syndrome), or Groups A, B, and C streptococci; ulcer related to infection by *Helicobacter pylori*; systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; atherosclerosis or cardiovascular disease related to infection by *Helicobacter pylori* or *Chiamydia pneumoniae*; bovine respiratory disease related to infection by *P. haemolytica, P. multocida, Mycoplasma bovis*, or Bordetella spp.; cow enteric disease related to infection by *E. coli* or protozoa; dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodysinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa; urinary tract infection in a dog or cat related to infection by *E. coli*; skin or soft tissue infection in a dog or cat related to infection by *Staph. epidermidis, Staph.*

*intermedius*, coagulase neg. Staph. or *P. multocida*; or dental or mouth infection in a dog or cat related to infection by Alcaligenes spp., Bacteroides spp., Clostridium spp., Enterobacter spp., Eubacterium, Peptostreptococcus, Porphyromonas, or Prevotella.

11. A methos of preparing a compound of the formula 1 or 5, or both 1 and 5

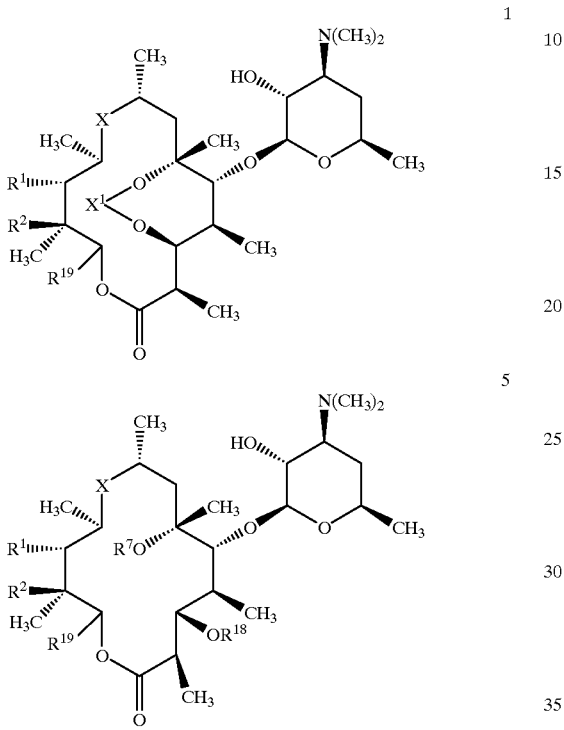

wherein X is —CH(—NR$^9$R$^{10}$)—, —CH(OR$^3$)—, —C(O)—, —CH$_2$NR$^6$—, —NR$^6$CH$_2$—, or —C(=NR$^5$)—, wherein the first dash of each of the foregoing X groups is attached to the C-10 carbon of the compounds of formulas 1 and 2 and the last dash of each group is attached to the C-8 carbon of the compounds of formulas 1 and 2;

X$^1$ is

R$^1$ and R$^2$ are each OH;
or R$^2$ is O and R$^1$ is X$^2$, and they are taken together as follows:

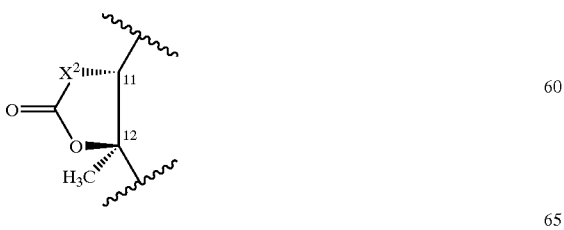

wherein X$^2$ is O, —N(R$^7$)—, or —N(NR$^7$R$^8$)—;

each R$^3$, R$^{3'}$, and R$^{3''}$ is independently selected from the group consisting of H, C$_1$–C$_6$ alkyl, —(CH$_2$)$_m$(C$_6$–C$_{10}$ aryl), and —(CH$_2$)$_m$(4–10 membered heterocyclic), wherein m is an integer ranging from 0 to 4 and the foregoing R$^3$ groups are optionally substituted by 1 to 3 R$^{13}$ groups;

R$^4$ is selected from the group of substituents provided in the definition of R$^3$ or R$^4$ is —OR$^7$;

or R$^3$ and R$^4$ are taken together with the carbon to which each is attached to form a ring defined by X$^3$, X$^4$ and X$^5$ as follows

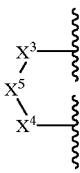

wherein X$^3$ and X$^4$ are each independently —(CHR$^{16}$)$_n$— wherein n is an integer ranging from 1 to 4;
X$^5$ is S, O, —CHR$^6$—, or —N(R$^6$)—,
R$^5$ is hydroxy, C$_1$–C$_6$ alkyl, C$_1$–C$_6$ alkoxy, —(CH$_2$)$_m$(C$_6$–C$_{10}$ aryl), —(CH$_2$)$_m$(4–10 membered heterocyclic), or —(CH$_2$)$_m$O(CH$_2$)$_z$OR$^7$, wherein m is an integer ranging from 0 to 4 and z is an integer ranging from 2 to 6, and the foregoing R$^5$ groups, except hydroxy, are optionally substituted by 1 to 3 R$^{13}$ groups;

R$^6$ is H, hydroxy, formyl, C$_1$–C$_{10}$ alkoxy, C$_1$–C$_{10}$ alkyl, C$_2$–C$_{10}$ alkenyl, —SO$_2$(C$_1$–C$_{10}$ alkyl), —(CH$_2$)$_m$C(O)CH$_2$OC(O)(C$_1$–C$_{10}$ alkyl), —(CH$_2$)$_m$C(O)(CH$_2$)$_t$NR$^{11}$R$^{12}$, —(CH$_2$)$_t$C(O)(C$_1$–C$_{10}$ alky), —(CH$_2$)$_m$C(O)(CH$_2$)$_t$C(O)(C$_1$–C$_{10}$ alkyl), —(CH$_2$)$_m$C(O)(CH$_2$)$_t$O(C$_1$–C$_{10}$ alkyl), —(CH$_2$)$_m$C(O)(CH$_2$)$_t$O(C$_2$–C$_{10}$ alkenyl), —(CH$_2$)$_t$(C$_6$–C$_{10}$ aryl), —(CH$_2$)$_t$(4–10 membered heterocyclic), —C(O)(CH$_2$)$_m$C(O)(CH$_2$)$_q$(C$_6$–C$_{10}$ aryl), —C(O)(CH$_2$)$_m$C(O)(CH$_2$)$_q$(4–10 membered heterocyclic), —(CH$_2$)$_m$C(O)(CH$_2$)$_q$(C$_6$–C$_{10}$ aryl), —(CH$_2$)$_m$C(O)(CH$_2$)$_q$(4–10 membered heterocyclic), —(CH$_2$)$_q$C(O)(CH$_2$)$_m$O(CH$_2$)$_t$(C$_6$–C$_{10}$ aryl), —(CH$_2$)$_q$C(O)(CH$_2$)$_m$O(CH$_2$)$_t$(4–1 0 membered heterocyclic), —(CH$_2$)$_t$O(CH$_2$)$_m$(C$_6$–C$_{10}$ aryl), —(CH$_2$)$_t$O(CH$_2$)$_m$(4–10 membered heterocyclic), —(CH$_2$)$_m$P(O)R$^3$R$^{16}$, —SO$_2$(CH$_2$)$_t$(C$_6$–C$_{10}$ aryl), or —SO$_2$(CH$_2$)$_t$(4–10 membered heterocylic), —(CH$_2$)$_m$C(S)(CH$_2$)$_t$NR$^{11}$R$^{12}$, wherein m is an integer ranging from 0 to 4, q and t are each independently an integer ranging from 0 to 5, the —(CH$_2$)$_q$— moiety of the above R$^6$ groups optionally includes a carbon-carbon double bond where q is 2 or greater, the heterocyclic moieties of the above R$^6$ groups optionally include an oxo (=O) group on the ring system, and the foregoing R$^6$ groups, except H, formyl and hydroxy, are optionally substituted by 1 to 3 R$^{13}$ groups;

each R$^7$ and R$^8$ is independently H or C$_1$–C$_6$ alkyl;
R$^9$ and R$^{10}$ are each independently selected from the group consisting of H, C$_1$–C$_6$ alkyl, —C(=NR$^5$)NR$^7$R$^8$, and —C(O)R$^7$, or R$^9$ and R$^{10}$ are taken together to form =CH(CH$_2$)$_m$(C$_6$–C$_{10}$ aryl), =CH(CH$_2$)$_m$(4–10 membered heterocyclic), =CR$^7$R$^8$, or =C(R$^7$)C(O)OR$^8$, wherein m is an integer ranging from 0 to 4, and the alkyl, aryl and heterocyclic moieties of the foregoing R$^9$ and R$^{10}$ groups are optionally substituted by 1 to 3 R$^{13}$ groups;

$R^{11}$ and $R^{12}$ are each independently selected from the group consisting of H, $C_1$–$C_{10}$ alkyl, $C_2$–$C_{10}$ alkenyl, —C(O)($C_1$–$C_{10}$ alkyl), —(CH$_2$)$_m$($C_6$–$C_{10}$ aryl), —C(O)(CH$_2$)$_m$($C_6$–$C_{10}$ aryl), —(CH$_2$)$_m$(4–10 membered heterocyclic), and —C(O)(CH$_2$)$_m$(4–10 membered heterocyclic), wherein m is an integer ranging from 0 to 4, and the foregoing $R^{11}$ and $R^{12}$ groups, except H, are optionally substituted by 1 to 3 $R^{13}$ groups;

each $R^{13}$ is independently selected from the group consisting of halo, cyano, nitro, trifluoromethyl, azido, —C(O)$R^{16}$, —C(O)O$R^{16}$, —OC(O)$R^{16}$, —OC(O)O$R^{16}$, —NR$^{14}$C(O)$R^{15}$, —C(O)NR$^{14}$R$^{15}$, —NR$^{14}$R$^{15}$, hydroxy, $C_1$–$C_6$ alkyl, —N(SO$_2$R$^{16}$)$_2$, —NR$^{14}$SO$_2$R$^{16}$, —S(O)$_j$($C_1$–$C_6$ alkyl) wherein j ranging from 0 to 2, $C_1$–$C_6$ alkoxy, —(CH$_2$)$_m$($C_6$–$C_{10}$ aryl), and —(CH$_2$)$_m$(4–10 membered heterocyclic), wherein m is an integer ranging from 0 to 4, and the alkyl, alkoxy, aryl and heterocyclic moieties of the above $R^{13}$ subsituents are optionally substituted by 1 to 3 substituents independently selected from halo, cyano, nitro, trifluoromethyl, azido, —C(O)$R^{16}$, —C(O)O$R^{16}$, —CO(O)$R^{16}$, —OC(O)O$R^{16}$, —NR$^{14}$C(O)$R^{15}$, —C(O)NR$^{14}$R$^{15}$, —NR$^{14}$R$^{15}$, hydroxy, $C_1$–$C_6$ alkyl, and $C_1$–C6 alkoxy;

each $R^{14}$ and $R^{15}$ is independently H, —OR$^7$, $C_1$–$C_6$ alkyl, —(CH$_2$)$_m$($C_6$–$C_{10}$ aryl), or —(CH$_2$)$_m$(4–10 membered heterocyclic), wherein m is an integer ranging from 0 to 4, with the proviso that where $R^{14}$ and $R^{15}$ are both attached to the same nitrogen, then $R^{14}$ and $R^{15}$ are not both —OR$^7$;

each $R^{16}$ is independently selected from the group consisting of H, $C_1$–$C_{10}$ alkyl, —(CH$_2$)$_m$($C_6$–$C_{10}$ aryl), and —(CH$_2$)$_m$(4–10 membered heterocyclic), wherein m is an integer ranging from 0 to 4;

$R^{18}$ is —C(R$^3$)=CR$^{3'}$R$^{3''}$ or a group of the formula

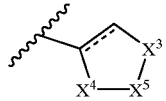

wherein the dashed line represents an optional double bond; and $R^{19}$ is ethyl, an alpha-branched $C_3$–$C_6$ alkyl, $C_2$–$C_6$ alkenyl, $C_2$–$C_6$ alkynyl, ($C_1$–$C_6$ alkoxy)$C_1$–$C_6$ alkyl, ($C_1$–$C_6$ alkylthio)$C_1$–$C_6$ alkyl, ($C_5$–C8 cycloalkyl)($C_2$–$C_5$ alpha branched alkyl)-, $C_3$–$C_8$ cycloalkyl, $C_5$–$C_8$ cycloalkenyl, 3–6 membered O or S containing heterocyclic group, or phenyl, wherein each of the foregoing $R^{19}$ groups may be substituted by 1 to 3 substituents independently selected from hydroxy, halo and $C_1$–$C_4$ alkyl;

which comprises treating a compound of the formula

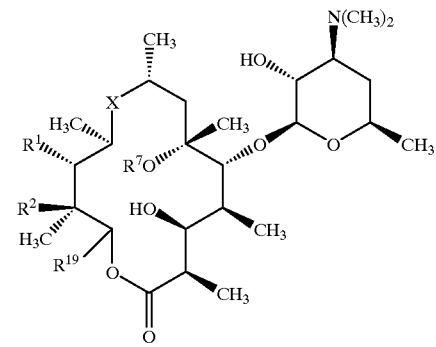

with a compound of the formula R$^3$C(O)R$^{3'}$, H$_3$CO(R$^3$)C=CR$^{3'}$R$^{3''}$ or

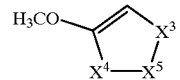

wherein R$^3$, R$^{3'}$, R$^{3''}$, X$^4$, X$^5$, and X$^3$ are as defined above, in an aprotic solvent in the presence of pyridinium p-toluenesulfonate or p-toluenesulfonic acid monohydrate, or both pyridinium p-toluenesulfonate and p-toluenesulfonic acid monohydrate.

* * * * *